(12) United States Patent
Wyand et al.

(10) Patent No.: US 11,173,199 B2
(45) Date of Patent: Nov. 16, 2021

(54) LOW CONTAMINANT COMPOSITIONS

(71) Applicant: ALOPEXX INC., Cambridge, MA (US)

(72) Inventors: Michael Wyand, Westport Point, MA (US); Suman Patel, Melourne, FL (US); Gerald F. Swiss, San Diego, CA (US)

(73) Assignee: ALOPEXX INC., Cambridge, MA (US)

( * ) Notice: Subject to any disclaimer, the term of this patent is extended or adjusted under 35 U.S.C. 154(b) by 0 days.

(21) Appl. No.: 16/823,290

(22) Filed: Mar. 18, 2020

(65) Prior Publication Data

US 2021/0283236 A1  Sep. 16, 2021

Related U.S. Application Data

(60) Provisional application No. 62/934,925, filed on Nov. 13, 2019.

(51) Int. Cl.
*A61K 39/08* (2006.01)
*A61K 47/64* (2017.01)
*A61K 31/7028* (2006.01)
*A61K 39/00* (2006.01)

(52) U.S. Cl.
CPC .......... *A61K 39/08* (2013.01); *A61K 31/7028* (2013.01); *A61K 47/6415* (2017.08); *A61K 2039/55583* (2013.01); *A61K 2039/6037* (2013.01)

(58) Field of Classification Search
None
See application file for complete search history.

(56) References Cited

U.S. PATENT DOCUMENTS

| | | | |
|---|---|---|---|
| 5,286,846 | A | 2/1994 | Inman et al. |
| 5,646,123 | A | 7/1997 | Ippolito et al. |
| 7,786,255 | B2 | 8/2010 | Pier et al. |
| 8,492,364 | B2 | 7/2013 | Pier et al. |
| 10,828,360 | B1 | 11/2020 | Wyand et al. |
| 2005/0118198 | A1 | 6/2005 | Pier et al. |
| 2010/0021503 | A1 | 1/2010 | Denoel et al. |
| 2015/0165016 | A1 | 6/2015 | Pier et al. |
| 2016/0375117 | A1 | 12/2016 | Pier et al. |
| 2017/0246285 | A1 | 8/2017 | Berti |
| 2019/0117754 | A1 | 4/2019 | Pier et al. |

FOREIGN PATENT DOCUMENTS

| | | |
|---|---|---|
| WO | WO-2004/043405 A2 | 5/2004 |
| WO | WO-2011/133227 A2 | 10/2011 |

OTHER PUBLICATIONS

U.S. Appl. No. 16/577,955, filed Sep. 20, 2019, Wyand et al.
U.S. Appl. No. 62/892,400, filed Aug. 27, 2019, Dabora.
U.S. Appl. No. 62/939,331, filed Nov. 22, 2019, Wyand et al.
U.S. Appl. No. 62/994,130, filed Mar. 24, 2020, Wyand et al.
"Biofilm." *Wikipedia: The Free Encyclopedia.* Wikimedia Foundation, Inc. Nov. 25, 2019. Web. Dec. 11, 2019. 24 pages. <en.wikipedia.org/wiki/Biofilm>.
Gening, M.L., et al. (2010). "Synthetic β-(1→6)-Linked N-Acetylated and Nonacetylated Oligoglucosamines Used to Produce Conjugate Vaccines for Bacterial Pathogens." *Infection and Immunity.* 78(2): 764-772.
Gening, M.L., et al. (2013, e-published Apr. 28, 2013). "Linear and cyclic oligo-β-(1→6)-D-glucosamines: Synthesis, conformations, and applications for design of a vaccine and oligodentate glycoconjugates." *Pure Appl. Chem.*,85(9):1879-1891.
Little, D.J. et al. (Sep. 11, 2015, e-published Jul. 22, 2015). "The Protein BpsB Is a Poly-β-1,6-N-acetyl-d-glucosamine Deacetylase Required for Biofilm Formation in *Bordetella bronchiseptica*," *J. Biol. Chem.* 290(37):22827-22840. Web. Dec. 6, 2019.
UniProt Protein Database, accession Q6TYB1; Q54067, "Poly-beta-1,6-N-acetyl-D-glucosamine N-deacetylase," Mar. 15, 2005, Entry version 63 (Nov. 13, 2019), retrieved from http://www.uniprot.org/uniprot/Q6TYB1. Retrieved Dec. 11, 2019. 2 pages.
International Search Report and Written Opinion issued in International Application No. PCT/US2020/048265, dated Jan. 28, 2021 (dated Jan. 28, 2021). 11 pages.
Abdelhameed, A. et al. (2012, e-published Jul. 16, 2012), "An asymmetric and slightly dimerized structure for the tetanus toxoid protein used in glycoconjugate vaccines." *Carbohydrate polymers*, 90(4), 1831-1835.
Dumpa, N. et al. (2019, e-published Jan. 4, 2019), "Stability of Vaccines." *AAPS PharmSciTech*, 20(2):42. 11 pages.. doi: 10.1208/s12249-018-1254-2. PMID: 30610415.
International Search Report and Written Opinion issued in International Application No. PCT/US2020/59959, dated Feb. 5, 2021 (dated Feb. 5, 2021). 10 pages.

*Primary Examiner* — Padmavathi Baskar
(74) *Attorney, Agent, or Firm* — Mintz, Levin, Cohn, Ferris, Glovsky and Popeo, P.C.

(57) ABSTRACT

Disclosed are antimicrobial vaccines comprising oligosaccharide β-(1→6)-glucosamine groups.

10 Claims, 3 Drawing Sheets

LOW CONTAMINANT COMPOSITIONS

FIELD OF THE INVENTION

This invention is directed to compositions comprising oligosaccharide β-(1→6)-glucosamine groups. These vaccine compositions that provide immunity against microbes possessing a cell wall structure that comprises polymeric N-acetyl-β-(1→6)-glucosamine structures wherein up to about 20 percent of said N-acetyl groups in the polymer are deacetylated ("PNAG structures").

STATE OF THE ART

Vaccines comprising oligosaccharide β-(1→6)-glucosamine antigens attached to a toxoid carrier through a linker are known. These vaccines generate antibodies in vivo that are cytotoxic to microbes that comprise PNAG structures in their cell wall. The so generated antibodies combine with complement and other components of the immune system to kill these microbes.

Vaccines that employ tetanus toxoid as the carrier having multiple copies of an oligosaccharide bound thereto are disclosed in U.S. Ser. No. 10/713,790 which is incorporated herein by reference in its entirety. Conventionally, attachment of oligosaccharide groups to the toxoid is through a covalent linker to reactive amino groups (e.g., —NH$_2$ as found on lysine residues) on the toxoid. Although the chemistry is well established, there are a number of complications in dealing with toxoid chemistry.

First, tetanus toxoid is prepared by treating tetanus toxin with a chemical such as formaldehyde that renders it non-toxic but still antigenic. Formaldehyde reacts with reactive amino groups on the toxin. In addition, amino acids such as glycine and lysine are added to stabilize the toxoid and inhibit reversion back to the toxin. Second, in addition to unreacted amounts of glycine and lysine, the manufacturing process results in fragments of the toxin/toxoid shedding into the toxoid composition. These fragments contain one or more amino groups.

Tetanus toxoid is then reacted with a spacer arm having two functional groups—a first functional group that combines to reactive amino groups on the toxoid and a second functional group, orthogonal to the first functional, that will react with a complementary functional group on the aglycon. In addition, the spacer arm increases the distance between the to be added oligosaccharide and the toxoid. The oligosaccharide aglycon is then combined with the tetanus toxoid loaded with spacer arms to form the vaccine compound. This is illustrated in the following reaction scheme:

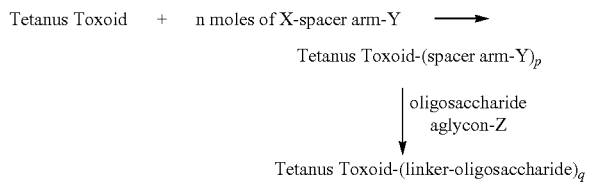

where n represents the number of moles of the bifunctional spacer arm, p represents the number of spacer arm-Y that are added to the toxoid and is not greater than n, and q represents the number of linker oligosaccharide groups combined with the tetanus toxoid provided that q cannot be greater than p. Note that the aglycon attached to the oligosaccharide and the spacer arm attached to the toxoid combine to form the linker.

One problem in the above reactions arises from the presence of these amino group containing contaminants in the toxoid composition during coupling of the oligosaccharide aglycon to the toxoid. Specifically, these amino groups can also react with the first reactive functionality on the spacer arm which then allows the second reactive functionality on the spacer arm to react with the complementary functionality on the aglycon resulting in both a loss of oligosaccharide aglycon as well as generation of undesired impurities in the vaccine composition. This is illustrated in the following reaction:

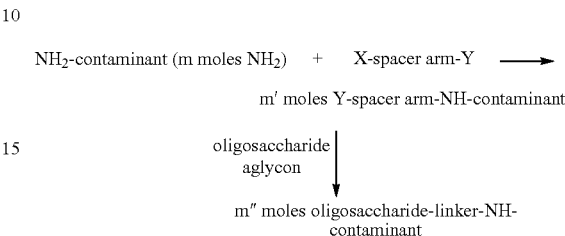

where m is the total content of amino groups, m' is a fraction of reacted amino groups and is less than the total amino content m; and m" is the fraction of reacted oligosaccharide linked to the contaminant and is less than m'.

These oligosaccharide-linker-NH-contaminants are undesirable especially those having a molecular weight of about 100,000 or less.

In addition, tetanus toxoid is prone to oligomerization such that the toxoid can exist in monomer, dimeric, trimeric and higher oligomeric form (e.g., 4-10 toxoid units). At increasingly higher oligomerization, the number of oligosaccharides capable of binding to the toxoid on a per monomer basis decreases as the available surface area on a per monomer basis decreases due oligomerization. Accordingly, oligomers of the toxoid such as trimeric and higher are less desirable. While tedious purification processes can provide monomeric tetanus toxoid, these processes are complicated by the fact that the monomers will tend to again oligomerize overtime.

SUMMARY OF THE INVENTION

In one embodiment, this invention provides for a vaccine composition comprising a pharmaceutically acceptable excipient and an effective amount of a vaccine that comprises at least 10 and preferably from about 10 to about 40 oligomeric-β-(1→6)-glucosamine groups linked units onto a tetanus toxoid carrier via a linker said oligomer comprises from 3 to 12 repeating β-(1→6)-glucosamine units provided that less than about 40 number percent of the total number of such units are N-acetylated wherein said vaccine composition comprises less than 3 percent of detectable impurities each having a molecular weight of less than 100,000;

further wherein said composition comprises monomeric and dimeric toxoid with less than 10 percent of detectable higher oligomers; and still further wherein said composition is maintained at a temperature sufficient to inhibit oligomerization of the toxoid while not inducing denaturation.

In one embodiment, this invention provides for a vaccine composition comprising a pharmaceutically acceptable excipient and an effective amount of a vaccine that comprises at least 25 and preferably from about 30 to about 40 oligomeric-β-(1→6)-glucosamine groups linked units onto a tetanus toxoid carrier via a linker said oligosaccharide groups comprise from 3 to 12 repeating β-(1→6)-glucosamine units provided that less than about 40 number percent of the total number of such units are N-acetylated wherein said vaccine composition comprises less than 3 weight percent of detectable impurities having a molecular weight of less than 50,000;

further wherein said composition comprises monomeric and dimeric toxoid with less than 5 percent of detectable higher oligomers, and still further wherein said composition is maintained at a temperature sufficient to inhibit oligomerization of the toxoid while not inducing denaturation.

In one embodiment, this invention is directed to vaccine compositions comprising a pharmaceutically acceptable excipient and an effective amount of a vaccine compound of formula I:

(A-B)$_x$-C    I where A comprises from 3 to 12 repeating β-(1→6)-glucosamine units or mixtures thereof having the formula:

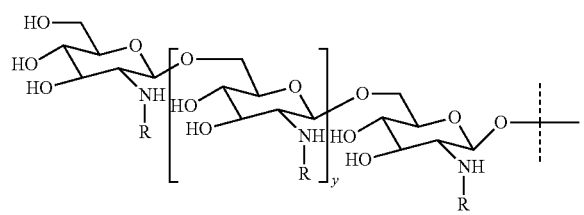

B is of the formula:

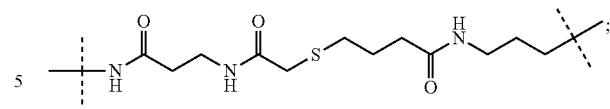

where the left side of the formula is attached to C and the right side is attached to A; and C is tetanus toxoid;
x is an integer from about 10 to about 40;
y is an integer from 1 to 10; and
R is hydrogen or acetyl provided that no more than 40% of the R groups are acetyl, wherein said composition comprises less than 3 percent of detectable impurities having a molecular weight of about 100,000 or less;

further wherein said composition comprises monomeric and dimeric toxoid with less than about 5 percent of detectable higher oligomers, still further wherein said composition is maintained at a temperature sufficient to inhibit oligomerization of the toxoid while not inducing denaturation.

In one embodiment of the vaccine composition describe above, the vaccine compound employed therein is represented by formula II:

(A'-B)$_x$-C    II where A' is a penta-β-(1→6)-glucosamine (carbohydrate ligand) group of the formula:

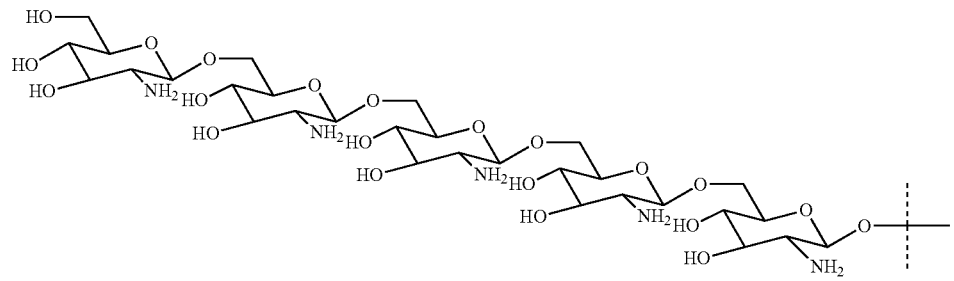

and B, C and x are as defined above.

In one embodiment, the vaccines of this invention provide for effective immunity to a patient from microbes comprising polymeric N-acetyl-β-(1→6)-glucosamine groups in their cell wall wherein up to about 20 percent of said N-acetyl groups in the polymer are deacetylated.

In one embodiment, this invention provides for a method to impart effective immunity to a patient from microbes comprising polymeric N-acetyl-β-(1→6)-glucosamine groups in their cell wall wherein up to about 20 percent of said N-acetyl groups in the polymer are deacetylated which method comprises administering a pharmaceutical composition as described herein to said patient.

Representative vaccine compounds of this invention are set forth in the table below:

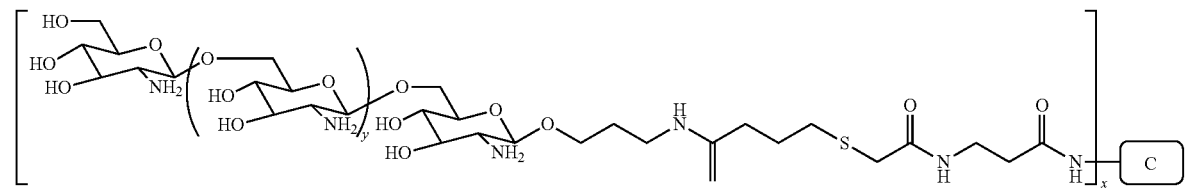

| Example | Y | C | Percent N-acetylated | x |
|---|---|---|---|---|
| A | 2 | Tetanus toxoid | 0% | 10 |
| B | 3 | Tetanus toxoid | 0% | 15 |
| C | 6 | Tetanus toxoid | 12.5% (1 of 8) | 20 |
| D | 10 | Tetanus toxoid | 25% (3 of 12) | 10 |
| E | 3 | Tetanus toxoid | 20% (1 of 5) | 20 |
| F | 4 | Tetanus toxoid | 33% (2 of 6) | 30 |
| G | 3 | Tetanus toxoid | 20% (2 of 5) | 35 |
| H | 3 | Tetanus toxoid | 0% | 40 |

In one embodiment, the compositions of this invention comprise no more about 0.5 weight percent of oligosaccharide-linked contaminants having a particle size of less than 1 micron wherein said weight percent is based on the weight of vaccine compound.

DETAILED DESCRIPTION OF THE INVENTION

Figure 1:
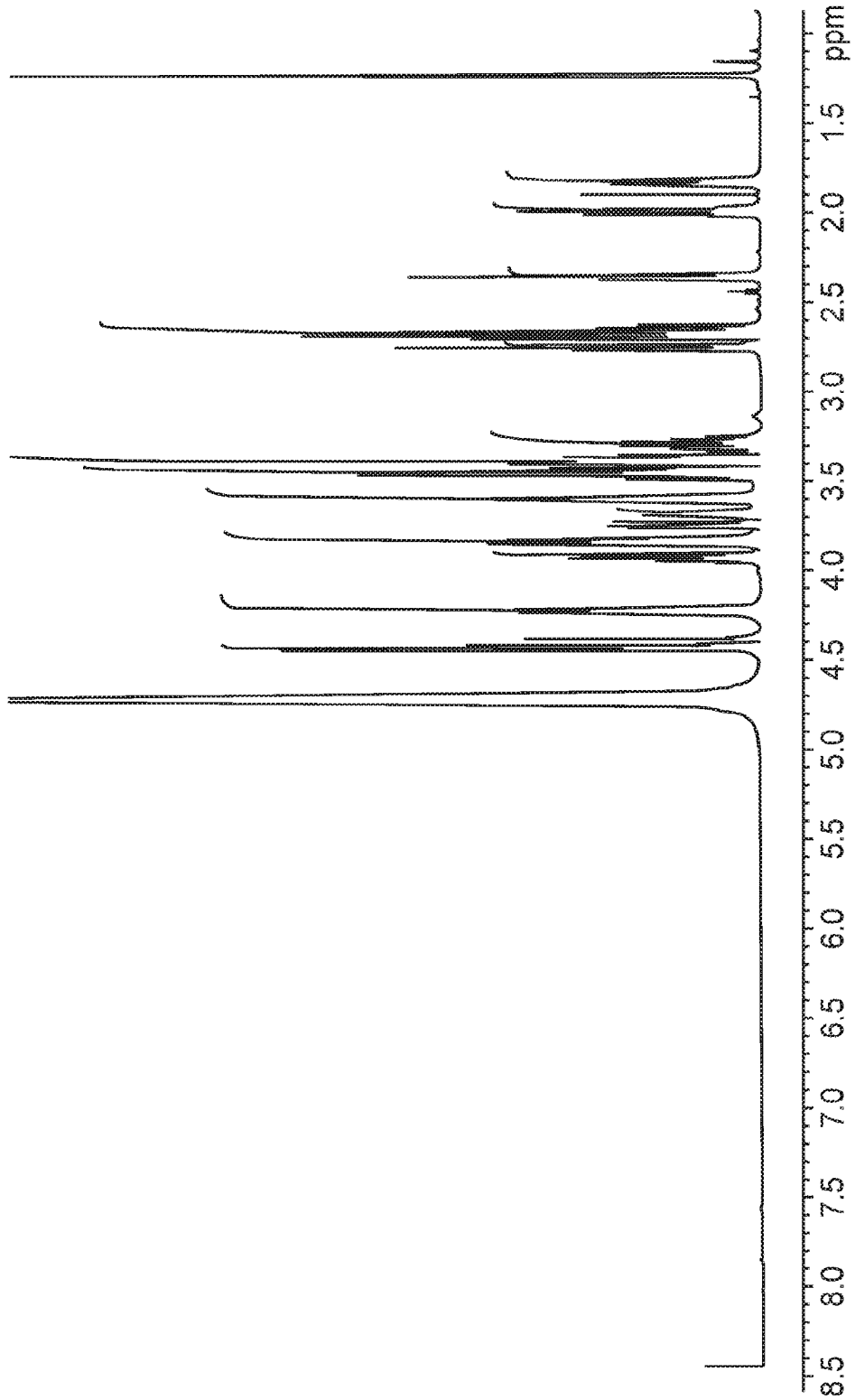
FIG. 1 illustrates the $^1$H NMR for compound 17 (as described below).

This invention provides for pharmaceutical compositions comprising oligosaccharide β-(1→6)-glucosamine groups.

The vaccine compositions described herein provide effective immunity to a patient against microbial infections wherein said microbe comprises oligomeric N-acetyl-β-(1→6)-glucosamine structures in its cell walls wherein up to about 20 percent of said N-acetyl groups in the polymer are deacetylated.

Prior to describing this invention in more detail, the following terms will first be defined. If a term used herein is not defined, it has its generally accepted scientific or medical meaning.

The terminology used herein is for the purpose of describing particular embodiments only and is not intended to be limiting of the invention. As used herein, the singular forms "a", "an" and "the" are intended to include the plural forms as well, unless the context clearly indicates otherwise.

"Optional" or "optionally" means that the subsequently described event or circumstance can or cannot occur, and that the description includes instances where the event or circumstance occurs and instances where it does not.

The term "about" when used before a numerical designation, e.g., temperature, time, amount, concentration, and such other, including a range, indicates approximations which may vary by (+) or (−) 10%, 5%, 1%, or any subrange or subvalue there between. Preferably, the term "about" when used with regard to a dose amount means that the dose may vary by +/−10%.

"Comprising" or "comprises" is intended to mean that the compositions and methods include the recited elements, but not excluding others. "Consisting essentially of" when used to define compositions and methods, shall mean excluding other elements of any essential significance to the combination for the stated purpose. Thus, a composition consisting essentially of the elements as defined herein would not exclude other materials or steps that do not materially affect the basic and novel characteristic(s) of the claimed invention. "Consisting of" shall mean excluding more than trace elements of other ingredients and substantial method steps. Embodiments defined by each of these transition terms are within the scope of this invention.

As used herein, "percent detectable impurities" is an area percent. This does not include higher oligomers. The assay to assess the area percent is set forth in Example 6 below. The impurities are assessed as % of total area attributable to them with, for example, size exclusion chromatographic analysis. The referenced impurities may be separated and controlled by size exclusion chromatography and by other molecular weight cut-off filtration processes. The buffers salts, pH and process conditions may be used to ensure desired characteristics, quality and stability.

As used herein, "inhibit oligomerization of the toxoid in the vaccine while not inducing denaturation," refers, in part, to operational parameters for working with monomeric and/or dimeric toxoid vaccines. For example, the monomer and/or dimeric toxoid may exhibit long term stability against oligomerization when the vaccine compositions disclosed herein are stored at temperature in a range from about 2° C. to about 8° C. Denaturation of the vaccine compositions disclosed herein may occur, in some embodiments, when the compositions are stored at 0° C., or lower. Likewise, oligomerization of monomeric and/or dimeric toxoid can occur if the vaccine composition is stored at temperatures above 8° C. or more likely above 20° C.

As used herein, a "detectable impurity" refers to low molecular weight impurities (molecular weight of less than 100,000) that arise from toxoid degradation and can be measured via chromatographic separation with a detector. In embodiments, the chromatographic separation may be by filtration, size exclusion chromatography and the like. Detectors may employ UV detection means, refractive index, or the like. Similarly, the "percent of detectable higher oligomers" may be determined in a similar fashion by chromatographic techniques coupled with detection.

As used herein, "oligosaccharide-linked and amino containing contaminant" refers to two forms of contaminant that may be formed due to the presence of trace amount of lower molecular weight impurities. Oligosaccharide-linked contaminants include adducts formed between degradation impurities present in toxoid preparations and the linking reagents used for oligosaccharide attachment to the toxoid. Thus, oligosaccharide-linked contaminants include amine-containing degradation products from toxoid preparation linked through one or more amino groups of the degradation product to a spacer arm that makes up a linker, and an oligosaccharide that ends up attached to the spacer arm distal to the amino group of the contaminant. These by-product adducts consume reagents intended to react with the monomeric and/or dimeric toxoid, thus depleting the supply of reagent. Any deficiency in reagent can lead to the second form of contaminant, namely "amino containing contaminants" which are unreacted amino groups that reside on the toxoid of the final vaccine composition. Embodiments herein are provided that minimize these products through phased filtration methods described herein.

The term "β-(1→6)-glucosamine unit" or "glucosamine unit" refers to individual glucosamine structures as follows:

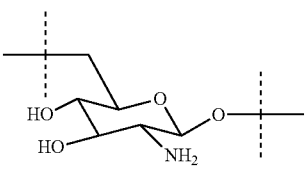

where he 6-hydroxyl group is condensed with the 1 hydroxyl group of the preceding glucosamine unit and where the dashed lines represent binding sites to the preceding and succeeding glucosamine units. When combined with another "β-(1→6)-glucosamine unit, the resulting disaccharide has the structure:

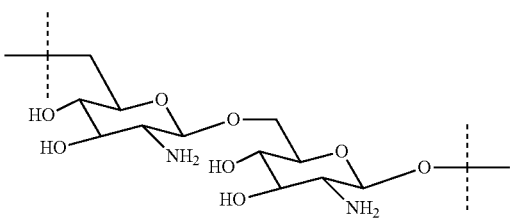

The term "β-(1→6)-glucosamine unit possessing an N-acetyl group refers to the structure:

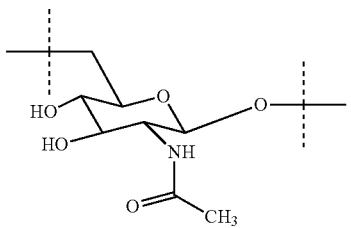

where the 6-hydroxyl group of a second unit is condensed with the 1-hydroxyl group of the proceeding glucosamine unit.

The term "oligosaccharide comprising a β-(1→6)-glucosamine group" refers to that group on the vaccine compound that mimics a portion of the cell wall of pathogenic bacteria which are defined to be "oligosaccharide β-(1→6)-glucosamine structures" (as defined below). Again, such groups are limited to 3 to 12 β-(1→6)-glucosamine units wherein up to 40% of said units can possess a N-acetyl group. In one embodiment, less than 30% of said β-(1→6)-glucosamine units are N-acetylated. In another embodiment, less than 20% of said β-(1→6)-glucosamine units are N-acetylated. Still, in another embodiment, less than 10% of said β-(1→6)-glucosamine units are N-acetylated. Yet still, in another embodiment, none of said β-(1→6)-glucosamine units are N-acetylated.

The term "oligosaccharide comprising N-acetyl β-(1→6)-glucosamine structures" or "polysaccharide comprising N-acetyl β-(1→6)-glucosamine structures" refers to those structures found in the cell wall of microbes wherein up to about 20 percent of said N-acetyl groups in the polymer are deacetylated. The microbial wall contains a large number of these structures that are conserved across many microbial lines. These structures are predominantly N-acetyl β-(1→6)-glucosamine but include regions of deacetylated saccharides due to the action of enzymes such as poly-beta-1,6-D-glucosamine-N-deacetylase. As such, the vaccines of this invention generate antibodies that comprise those that target such deacetylated oligosaccharide regions. Without being limited to any theory, antibodies against such deacetylated saccharides are cytotoxic in vivo against such microbes.

The terms "vaccine composition" or "pharmaceutical compositions" as used herein refers to pharmaceutical compositions comprising compounds of formula I and II above including adjuvants and a pharmaceutical carrier. These compositions also comprise limited amounts of oligosaccharide-linked and amino containing contaminants including those wherein the amount of such contaminants is no more than 3 percent, preferably, less than 2 percent and, more preferably, less than 1 percent. These compositions provide effective immunity against any microbe that comprises oligosaccharides/polysacchariodes having N-acetyl-β-(1→6)-glucosamine structures in its cell wall. Thus, unlike classic vaccines that vaccinate against a single bacteria, the vaccine compositions described herein are capable of providing effective immunity against any microbe possessing the oligosaccharide structure described herein. Such microbes include, without limitation, Gram-positive bacteria, Gram-negative bacteria, antibiotic resistant bacteria (e.g., methicillin resistant *Staphylococcus aureus*), fungi, and the like.

The term "effective immunity" as used herein refers to the ability of a defined amount of the vaccine composition to generate an antibody response in vivo that is sufficient to treat, prevent, or ameliorate a microbial infection wherein said microbe contains oligosaccharides/polysaccharides comprising N-acetyl-β-(1→6)-glucosamine in its cell walls.

The vaccines compounds refer to the compounds of formula I and II. These compounds may exist as solvates, especially hydrates. Hydrates may form during manufacture of the compounds or compositions comprising the compounds, or hydrates may form over time due to the hygroscopic nature of the compounds. Compounds of this invention may exist as organic solvates as well, including DMF, ether, and alcohol solvates among others. The identification and preparation of any particular solvate is within the skill of the ordinary artisan of synthetic organic or medicinal chemistry.

The term "toxoid" refers to monomeric and oligomeric tetanus toxoid forms. The presence of oligomeric tetanus toxoid components reduces the average number of exposed reaction amino groups as the surface area of each monomeric toxoid in the oligomer is reduced by oligomerization. In turn, this results in lower factors for the oligosaccharide bound to the toxoid. Vaccine compositions disclosed herein comprise toxoids that are in monomeric and/or dimeric form. In embodiments, a ratio of monomer to dimer is in a range from about 10:1 to about 1:10, or from about 5:1 to about 1:5, or from about 2:1 to about 1:2.

"Subject" refers to a mammal. The mammal can be a human or non-human mammal but preferably is a human.

"Treating" or "treatment" of a disease or disorder in a subject refers to 1) preventing the disease or disorder from occurring in a subject that is predisposed or does not yet display symptoms of the disease or disorder; 2) inhibiting the disease or disorder or arresting its development; or 3) ameliorating or causing regression of the disease or disorder.

"Effective amount" refers to the amount of a vaccine composition of this invention that is sufficient to treat the disease or disorder afflicting a subject or to prevent such a disease or disorder from arising in said subject or patient.

"Reactive amino functional group" refers to a primary amino groups (—NH$_2$) that are found on lysine and guanidine side chains of tetanus toxoid but do not include amido (—NHC(O)—) groups found in peptide linkages or amido side chains of tetanus toxoid such as that found in glutamine.

"Low molecular weight amino compounds" refer to amino containing compounds that are present as contaminants in a tetanus toxoid composition including fragments of the toxoid, buffers containing amino groups, reaction quenchers such as lysine, glycine, ammonium sulfate, and the like, toxin detoxifying agents such as formalin, and other amino containing reagents that have been in contact with the tetanus toxoid. Typically, such low molecular weight reactive amino compounds have a molecular weight of less than about 100,000 and preferably less than 10,000.

General Synthetic Methods

The compounds of this invention can be prepared from readily available starting materials using the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in T. W. Greene and P. G. M. Wuts, *Protecting Groups in Organic Synthesis*, Third Edition, Wiley, New York, 1999, and references cited therein.

The starting materials for the following reactions are generally known compounds or can be prepared by known procedures or obvious modifications thereof. For example, many of the starting materials are available from commercial suppliers such as SigmaAldrich (St. Louis, Mo., USA), Bachem (Torrance, Calif., USA), Emka-Chemce (St. Louis, Mo., USA). Others may be prepared by procedures, or obvious modifications thereof, described in standard reference texts such as *Fieser and Fieser's Reagents for Organic Synthesis*, Volumes 1-15 (John Wiley, and Sons, 1991), *Rodd's Chemistry of Carbon Compounds*, Volumes 1-5, and Supplementals (Elsevier Science Publishers, 1989), *Organic Reactions*, Volumes 1-40 (John Wiley, and Sons, 1991), *March's Advanced Organic Chemistry*, (John Wiley, and Sons, 5th Edition, 2001), and *Larock's Comprehensive Organic Transformations* (VCH Publishers Inc., 1989).

Synthesis of Representative Vaccine Compounds of the Invention

The general synthesis of the vaccine compounds of this invention are known in the art and are disclosed in U.S. patent application Ser. No. 10/713,790 as well as in U.S. Pat. Nos. 7,786,255 and 8,492,364 each of which are incorporated herein by reference in its entirety.

In one embodiment for the vaccine compounds described herein, the β-(1→6)-glucosamine group is limited to from 4 to 6 units and preferably 5 units, e.g., y=2 to 4 in formulas I.

In some embodiments, the compounds are homogeneous in that y is a single integer selected from 1 to 10, inclusive. Thus, compounds disclosed herein may be designed to be homogeneous with y=to 1, 2, 3, 4, 5, 6, 7, 8, 9, or 10. In some embodiments, compounds of formula I may be designed to be heterogeneous with two or more values for y, such as a mixture of y=1 and 2, or y=2 and y=3, or y=3 and y=4, or y=4 and y=5, or y=5 and y=6, or y=6 and y=7, or y=7 and y=8, or y=8 and y=9, or y=9 and y=10. Such pairings of y need not be contiguous. Thus, compounds may include mixtures of y=1 and y=3, or y=1 and y=4, or y=2 and y=4, or y=2 and y=5, and so on in any combination of 2 or more different values for y. In some embodiments, compounds may be heterogeneous with 3 or more values for y, or 4 or more values for y, or 5 or more values for y, up to all 10 different values for y. In some embodiments, each incidence of y is independent in compounds of formula I.

In some embodiments, two or more compounds of formula I may be used in a pharmaceutical composition in which each individual compound of formula I is homogeneous in y, while the other compound(s) of formula I has/have a different y value. In such an embodiment, the homogenous compounds employed are simply mixed together at a defined weight percentage. For example, a pharmaceutical composition may comprise a compound of formula I in which y=1 in a mixture with a compound of formula I in which y is 2. When pharmaceutical compositions or methods include a heterogenous mixture of compounds of formula I, the mixture can be one that is defined in terms of the relative weight percentages of each compound of formula I. For example, the mixture can include 50 weight percent of a compound of formula I with y equal to 1 and 50 weight percent of a compound of formula I with y equal to 2. Any combination of compounds totaling 100% is contemplated, for example, 1, 2, 3 4, 5 or more compounds each with a different y value can be mixed with known relative weight percent totaling 100%. Accordingly, any combination of weight percentages of compounds of formula I can be used in the pharmaceutical compositions and methods disclosed herein. Thus, for a combination of two compounds of formula I, the percentage can be expressed as a ratio of the two compounds and can be in any range from 0.1:99.9 to 99.9:0.1, inclusive, and any values there between, such as 1:99, 5:95, 10:90, 15:85, 20:80, and so on up to 99:1, including fractional values. Similarly, when 3, 4, 5, or more compounds of formula I in a pharmaceutical composition are used, the relative weight percentages of each compound can vary from 0.1 weight percent to a maximum of 99 weight percent provided that the total amount of the different compounds of formula I add up to 100%.

The formation of the linker group is achieved by art recognized synthetic techniques exemplified but not limited to those found in U.S. Pat. No. 8,492,364 and the examples below. In one embodiment, a first portion of the aglycon is attached to the reducing β-(1→6)-glucosamine unit retains a thiol (—SH) group as depicted below in formula III:

III where y is an integer from 1 to 10 and optionally no more than 40% of the amino groups are N-acetyl groups.

Preparation of Tetanus Toxoid

Tetanus toxoid is commercially available in varying degrees of purity where the toxoid invariably contains significant amounts of amino derived contaminants. These contaminants include fragments of the toxoid released by enzymatic or hydrolytic processes that contain amino functionalities as well as amino derived contaminants from unreacted glycine and arginine added during conversion of the toxin to the toxoid.

In addition to low molecular weight contaminants, an initial toxoid preparation may contain varying amounts of toxoid monomer, dimer, trimer and higher oligomers. When present in the toxoid preparation, oligomers comprising three or more monomers units compromise the ability to generate high loading factors of oligosaccharide. The loading factor is the number of units of oligosaccharide that are attached to a given monomer or dimer toxoid unit. It was surprisingly found that compositions of tetanus toxoid monomer and dimer allow for suitable loading factors obviating the need for separating monomer toxoid from dimeric toxoid. However, higher oligomers should be removed and in embodiments, higher oligomers should make up less than 5% of detectable higher oliogmers. The higher oligomers and low molecular weight contaminants can be removed through phased (or sequenced) filtrations, while providing a product having acceptable loading factors. In embodiments, purified toxoid preparations disclosed herein have loading factors of at least 25, and preferably at least 30. Lower loading factors are often the result of impurities reacting with oligosaccharide linking chemistry, thereby reducing the loading factor based on a stoichiometry of using a 35-fold excess of linking reagents relative to theoretical available sites for reaction on monomer plus dimer toxoid. Note, the issue of impurity presence is not simply solved by use of very large excesses of reagents. This is because it is both not economical and can result in intractable purification issues due to non-specific binding of oligosaccharide reagents to the toxoids.

In embodiments, methods are provided that employ phased filtrations to minimize both high molecular weight impurities that include higher oligomers of the toxoids and low molecular weight impurities that include toxoid degradation products. In embodiments, methods of phased filtration include filtering with one or more 3 to 5 micron pore size filters. These filters capture higher oligomers while passing monomers and dimers of the toxoid. In embodiments, such filtrations can be phased in the sense that a first filtration can be performed, for example, with a 5 micron filter, and then filtered through a 4 micron filter, and then a 3 micron filter. At 3 microns or more, it is expected that the majority of the dimer and monomer of the toxoid will pass through the filter, while the filter material traps the higher oligomers. Without being bound by theory it is postulated that filters having a 3 micron pore size or more will allow passage of the toxoid monomer or and some of the dimer because the monomer has been characterized as being about 2.5 microns long and about 0.5 microns wide.

In another filtration phase, low molecular weight impurities may be removed by using a filter that is 2.5 microns or less in pore size. In embodiments, the low molecular weight impurities are removed by passing the toxoid mixture through, e.g., a 2.5 micron pore size filter, where the monomer and dimer forms of the toxoid remain on the filter and low molecular weight impurities pass through the filter. In embodiments, the second phase to remove low molecular weight impurities comprises the use of a 2 micron filter, or in other embodiments a 1.5 micron filter. In embodiments, the pore size to remove low molecular weight impurities can also be phased, such as decreasing pore size from 2.5 microns down to 1.5 microns.

In embodiments, both phases of filtration to remove high and low molecular weight impurities can be performed prior to performing any functionalization chemistry to generate oligosaccharide-toxoid covalent adducts. Accordingly, in embodiments, a method of making a vaccine composition disclosed herein comprises passing a toxoid preparation through a first filter to remove higher oligomeric impurities wherein the dimeric and monomeric toxoid pass through the first filter, then after the passing through the first filter, passing the toxoid preparation through a second filter to remove low molecular weight impurities, wherein the monomeric and dimer toxoids are held on the filter and the smaller molecular weight impurities pass through the filter. In embodiments, after both filters have been used, the monomeric and dimeric toxoid mixture is reacted with a spacer arm that will generate a linker to which oligosaccharide may then be attached covalently. Filters having the appropriate pore size are well known in the art and are commercially available from Spherotech, Inc., Lake Forest, Ill., USA, www.spherotech.com/contact.htm.

In embodiments, the low molecular weight impurities may be removed first by using the smaller filter pore size, followed by removal of higher molecular weight impurities with the larger filter size.

In embodiments, reaction chemistries to link oligosaccharides can be performed between any filtrations step. For example, in embodiments, a first filtration can be performed to remove small impurities and the higher oligomers along with monomer and dimer may be reacted with spacer arm and then oligosaccharide attached. The second phase filtration can then be carried out on the adduct to remove higher oligomers. Similarly, the higher molecular weight impurities alone may be removed, followed by oligosaccharide adduct formation, and then the adduct purified with second phase filtration of the lower molecular weight impurities. Those skilled in the art will appreciate, however, that by removing low and high molecular weight impurities prior to oligosaccharide attachment chemistry will maximize the efficacy of reagent reaction where it is desired, namely on the amino groups of the monomeric and/or dimeric toxoid.

As will further be appreciated by those skilled in the art, the oligosaccharide attachment described herein is performed in two steps and the phased filtrations may be performed before and/or after the first step that attaches the spacer arm. Thus, the spacer arm may be attached after either a high molecular weight filtration, a low molecular weight filtration, or both. Thus, the final oligosaccharide attachment chemistry may follow any intervening filtrations step. The amino groups of the contaminants initially react with the spacer as described above to form an intermediate that is reactive with the aglycon also as described above to form an amino derived contaminant that contains an oligosaccharide. These contaminants can populate the vaccine composition remnant in amounts typically ranging up to 20 weight percent based on the weight of the toxoid.

The second portion of the linker is attached to the tetanus toxoid in the following manner as depicted in formula IV.

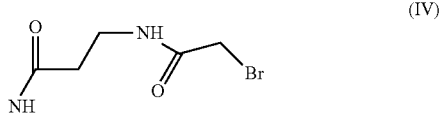

(IV)

In this formula, separate parts of tetanus toxoid are depicted by squiggly lines and are only illustrative in nature and are not intended to provide a complete structure of the toxoid. Any disulfide bridge is represented by a single line connecting the parts. For the sake of clarity, only a single second portion of the linker is illustrated whereas there are multiple such second portions covalently attached to amino groups found on the toxoid.

When the first and second portions of the linker are combined under coupling conditions, a thioether linkage is formed. The reaction is conducted in an inert diluent optionally in the presence of a base so as to scavenge the acid generated. The thioether linkage connects the first and second portions of the linker thereby providing for covalent linkage of the tetanus toxoid to the oligosaccharide β-(1→6)-glucosamine group through the combined linker as illustrated below for a vaccine compound where y is as defined herein.

wherein no more than 40% of the amino groups are optionally N-acetyl groups.

It being understood that the number of β-(1→6)-glucosamine group-linker-groups attached to the tentatus toxoid are stoichiometrically controlled so that about 31 to about 39 of such groups are bound to the toxoid thereby providing for the vaccine compounds of this invention.

Methods, Utility and Pharmaceutical Compositions

The vaccine compositions of this invention are capable of initiating an effective immune response against microbes that possess PNAG oligosaccharide β-(1→6)-glucosamine structures in their cell walls. After inoculation of a patient, an effective immune response develops about 4 weeks later. After an effective immune response develops, the patient is provided with protection against subsequent microbial infections wherein the offending microbes have cell walls comprising PNAG.

When so used, a vaccine composition of this invention is administered to patients at risk of a microbial infection arising from such microbes. Such patients include, by way of example only, those who are elderly, those with upcoming elected surgeries, those traveling to destinations where there is an outbreak of microbial infections, and the like. The vaccine is typically administered to an immune competent patient intramuscularly with a suitable adjuvant to enhance the immune response. After the latency period has passed, the patient has acquired natural immunity against such microbes. Such immune competent patients have an effective immune system that can generate an immune response to an antigen. Preferably, such patients have active white blood count (WBC) of at least about 1000 WBC per microliter, preferably at least about 1500 WBC per microliter, more preferably at least about 2000 WBC per microliter, even more preferably, about 3000 WBC per microliter and, most preferably, about 4000 WBC per microliter.

In another embodiment, the vaccine compositions of this invention can be used therapeutically particularly when the microbial infection is localized and/or non-life threatening. In such a case, a vaccine composition of this invention is administered to patients suffering from a microbial infection arising from such microbes. The vaccine is typically administered to an immune competent patient intramuscularly with a suitable adjuvant to enhance the immune response. Upon administration, effective immunity is generated within about

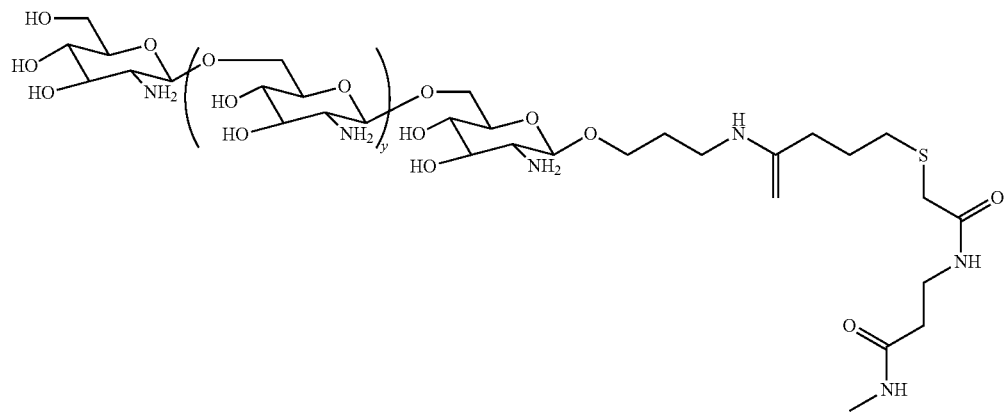

4 weeks. If the patient is still suffering from the infection, the natural immunity arising from the vaccine facilitates recovery.

When so used, the vaccine compositions of this invention are administered in a therapeutically effective amount by any of the accepted modes of administration for agents that serve similar utilities. The actual amount of the vaccine compound of this invention, i.e., the active ingredient, will depend upon numerous factors such as the severity of the disease to be treated, the age and relative health of the subject, the potency of the vaccine compound used, the route and form of administration, and other factors well-known to the skilled artisan.

An effective amount or a therapeutically effective amount of a vaccine compound of this invention, refers to that amount of vaccine compound that results in a sufficient titer of antibodies so as to ameliorate symptoms or a prolongation of survival in a subject. Toxicity and therapeutic efficacy of such vaccine compounds and vaccine compositions can be determined by standard pharmaceutical procedures in cell cultures or experimental animals.

The vaccine compositions described herein are typically administered as an injectable sterile aqueous composition that comprise one or more conventional components well known in the art including, by way of example only, adjuvants, stabilizers, preservatives and the like.

Combinations

The vaccine compounds and compositions of this invention can be used in conjunction with other therapeutic compounds or other appropriate agents as deemed suitable by the attending clinician. In selected cases, the vaccine compound of this invention can be concurrently administered with antibiotics for treating a bacterial infection as well as agents that enhance the immune response induced by the vaccine compound and/or composition. In the case of antibiotics, the selection of the appropriate antibiotic or cocktail of antibiotics and the amount to be administered to the patient is well within the skill of the attending physician based on the specifics of the offending bacteria, the extent of bacterial infection, the age, weight, and otherwise relative health of the patient. As is appropriate, the attending physician may co-administer an immune boosting drug or adjuvant in combination with the vaccines described herein.

The vaccine compositions of the invention may be administered with an adjuvant that potentiates the immune response to the antigen in the patient. Adjuvants include but are not limited to aluminum compounds such as gels, aluminum hydroxide and aluminum phosphate, and Freund's complete or incomplete adjuvant (e.g., in which the antigen is incorporated in the aqueous phase of a stabilized water in paraffin oil emulsion. As is apparent, the paraffin oil can be replaced with other types of oils such as squalene or peanut oil. Other materials with adjuvant properties include BCG (attenuated *Mycobacterium tuberculosis*) calcium phosphate, levamisole, isoprinosine, polyanions (e.g., polyA:U), lentinan, pertussis toxin, lipid A, Saponins, QS-21 and peptides, e.g., muramyl dipeptide, and immuno stimulatory oligonucleotides such as CpG oligonucleotides. Rare earth salts, e.g., lanthanum and cerium, may also be used as adjuvants. The amount of adjuvant used depends on the subject being treated and the particular antigen used and can readily determined by one skilled in the art.

EXAMPLES

This invention is further understood by reference to the following examples, which are intended to be purely exemplary of this invention. This invention is not limited in scope by the exemplified embodiments, which are intended as illustrations of single aspects of this invention only. Any methods that are functionally equivalent are within the scope of this invention. Various modifications of this invention in addition to those described herein will become apparent to those skilled in the art from the foregoing description and accompanying figures. Such modifications fall within the scope of the appended claims.

The following terms are used herein and have the following meanings. If not defined, the abbreviation has its conventionally recognized definition.

Å=Angstroms
aq.=aqueous
Biotage=Biotage, Div. Dyax Corp., Charlottesville, Va., USA
bp=boiling point
CAD=charged aerosol detector
DCM=dichloromethane
deg=degree
DMSO=dimethylsulfoxide
eq.=equivalents
EtOAc=ethyl acetate
FEP=fluorinated ethylene propylene
g=gram
$H^1$-NMR=proton nuclear magnetic resonance
h=hour
HDPE=high density polyethylene
HPLC=high performance liquid chromatography
MeCN=acetonitrile
kg=kilogram
mbar=millibar
MeOH=methanol
mg=milligram
mL=milliliter
mM=millimolar
mmol=millimole
N=Normal
NBS=N-bromosuccinimide
NIS=N-iodosuccinimide
NMT=N-methyltryptamine
PP=polypropylene
qHNMR=quantitative proton nuclear magnetic resonance
RBF=round bottom flask
RO=reverse osmosis
SEC HPLC=size exclusion chromatography HPLC
SIM=secondary ion mass
TCEP=(tris(2-carboxyethyl)phosphine
TLC=thin layer chromatography
TMSOTf=methanesulfonic acid, 1,1,1-trifluoro-,trimethylsilyl ester
TT=tetanus toxoid
µL=microliter
µM=microns
w/w=weight to weight
w/v=weight to volume Example 1—Tentanus Toxoid Phased Fitration Samples of crude tetanus toxoid preparations comprising monomeric and dimeric toxoid are first passed through a 3 to 5 micron filter to remove higher oligomers. This may be performed in phases of decreasing filter pore size. Thus, the toxoid preparation can be passed through a 5 micron filter, then a 3 micron filter. Alternatively, the toxoid preparation may be passed through a 5 micron filter, then 4 micron filter, then a 3 micron filter. The efficacy of a 5 micron filtration is assessed by light scattering techniques which can be used to detect the presence of higher oligomers. As needed, a stepped filtration is added to remove further higher oligomers. The resulting filtrate contains the monomer and dimeric toxoid. Where the chemistry for attachment of oligosaccharide follows complete purification, the filtrate is then passed through a 2.5 micron filter to allow isolation of the monomer and dimer toxoid as a filter cake, while low molecular weight impurities pass through with the filtrate. At each filtration step (high and low molecular weight), a rinse of the filter cake can be performed. c Example 2—Attachment of SBAP to TT Monomer Step 1: Preparation of N-BABA

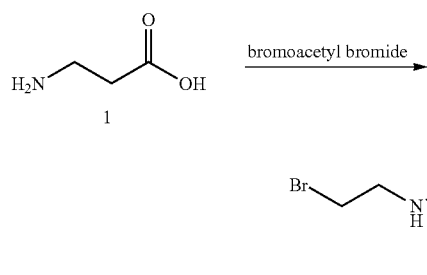

Commercially available beta-alanine, compound 1, is converted to N-BABA (bromoacetyl-β-alanine), compound 2, by reaction with at least a stoichiometric amount of commercially available bromoacetyl bromide. In a first container, β-alanine is combined into water with sodium bicarbonate or other suitable base to scavenge the acid that will be generated during the reaction. The aqueous solution is mixed at about 20±5° C. until a solution is obtained. The solution is then maintained at about 5±5° C. In a separate container, the requisite amount of bromoacetyl bromide is added followed by the addition of dichloromethane. The contents of the both containers are combined. After reaction completion, 6N HCl is added and mixed to a pH approximately 2. The resulting N-BABA is extracted from the solution by a suitable solvent such as ethyl acetate. The organic layer is concentrated under conventional conditions such as under vacuum at an elevated temperature such as 60° C. Heptane is then added to precipitate N-BABA that is then collected on a filter and dried in a vacuum oven at 40° C. This product is used as is in the next step.

Step 2: Preparation of SBAP

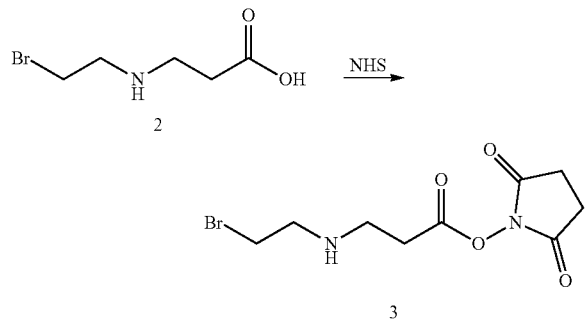

N-BABA, compound 2, is reacted with N-hydroxysuccinimide (NHS) under conventional conditions well known in the art to generate SBAP, compound 3. Specially, N-BABA is combined with at least a stoichiometric amount of NHS in a suitable inert solvent such as methanol, ethanol, isopropanol and the like. The resulting solution is stirred at about 20±5° C. until a clear solution is obtained. N-Diisopropylcarbodiimide is then added to the reaction mixture and mix with the generation of solids. The system is then cooled to 0±5° C. and resulting SBAP is provided by filtration. Further purification entails prechilling a mixture of isopropanol and heptanes and washing the filter cakes followed by drying wet cake in a vacuum oven at about 30° C. The resulting SBAP is used as is in the coupling reaction with the TT monomer.

Alternatively, SBAP can be prepared in the manner set forth in U.S. Pat. No. 5,286,846, which patent is incorporated herein by reference in its entirety. Specifically, the method described therein is provided by the following synthetic scheme:

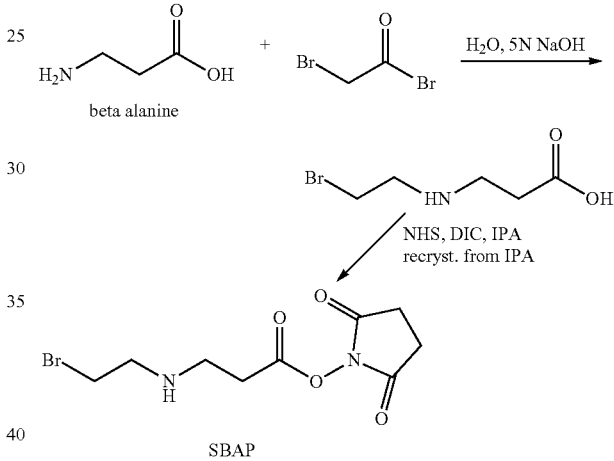

Step 3—Conjugation

Purified TT monomer, as described above, contains 43 lysine residues/mole as quantified by a free amine assay. Reaction of TT monomer with increasing concentrations of SBAP from 0 to 170 molar equivalents led to a corresponding decrease in the free amine content over the range 15-110 molar equivalents of SBAP. A steady state conversion was achieved at SBAP charges >110 equivalents. Assuming that the loss of free amines is directly proportional to loading of SBAP linker, the linker density at saturation was estimated to be 43 moles SBAP/TT monomer. The monomer/aggregate content of the linker TT/monomer intermediate and protein concentration at each titration point was also assessed. The monomer content prior to linker addition was 99.7 percent and addition of increasing amounts of SBAP linker did not significantly change the monomer level (no aggregate detected). Also, the recover of protein across the titration steps was similar. Based on this collective data, a value of 110 molar equivalents of SBAP for 1 hour at ambient temperature was selected as appropriate reaction conditions for all subsequent syntheses.

Example 3—Oligosaccharide Synthesis

Synthesis of Building Blocks

The reaction scheme below illustrates for the synthetic steps used to prepare compounds 3, 5 and 8 that are elaborated upon below.

dichloromethane (50 mL) and added to the reactor, rinsed with dichloromethane (50 mL) and added to vessel. The mixture was stirred at 20° C. for 2 h. The reaction was checked by TLC for residual C. Mobile phase was toluene: ethyl acetate (3:1, v/v), Product Rf~0.45, C Rf~0.3 with UV visualisation. If significant amounts of C were present extended reaction time was required.

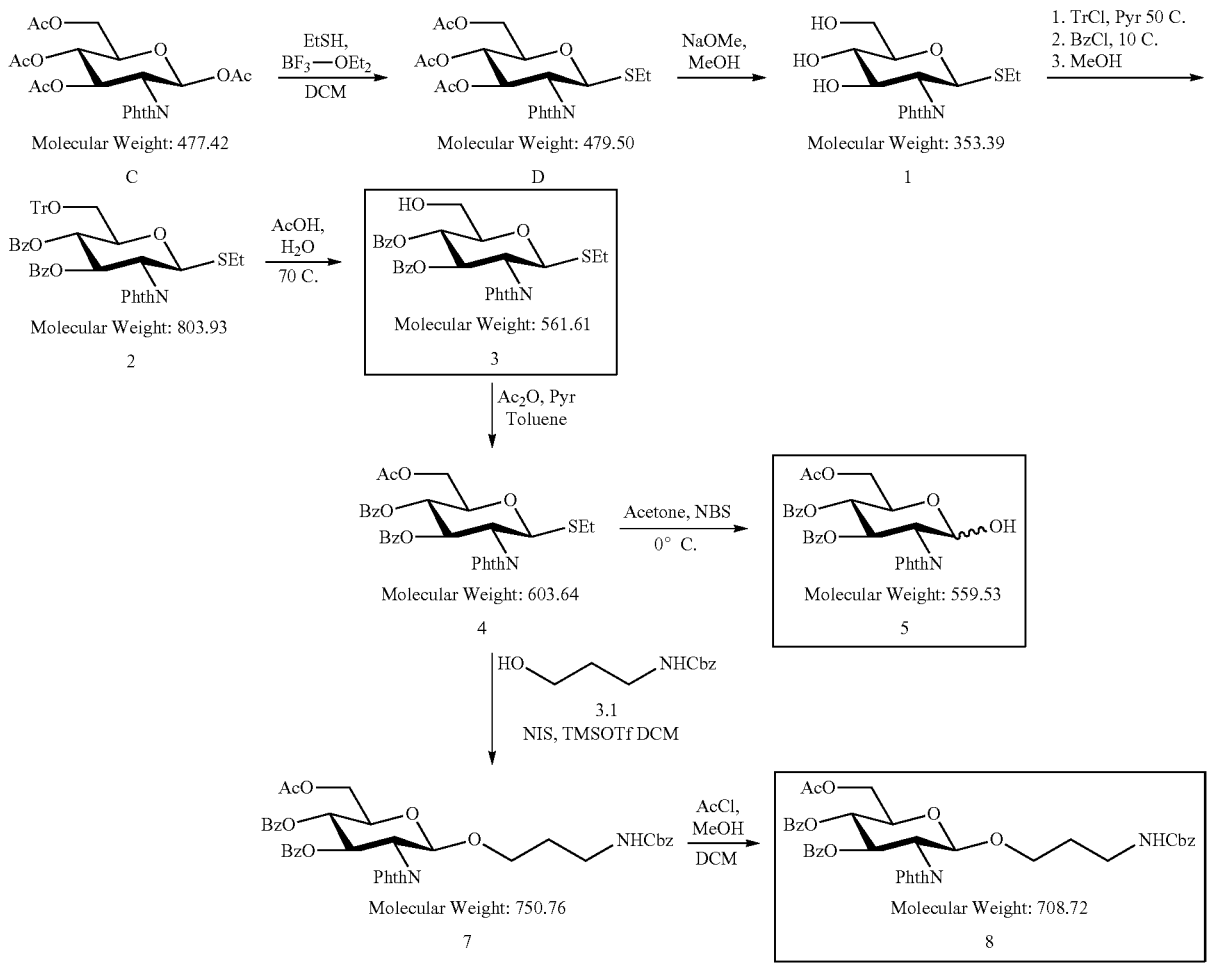

Commercially available 1,3,4,6-Tetra-O-acetyl-2-deoxy-2-N-phthalimido-β-D-glucopyranoside, compound C, (120.6 g, 252.6 mmol) and toluene (200 mL) were charged to a 1 L Büchi flask and rotated at 40° C. until dissolved (<5 minutes). The solvents were evaporated and to provide for a foam. Toluene (200 mL) was charged to the flask and rotated at 40° C. until dissolved (<5 minutes). The solvents were evaporated again until dry. A crystalline solid formed, sticking to the walls. Dichloromethane (800 mL) was charged to the flask and rotated at ambient until dissolved; the resulting dark brown solution was charged to a 5 L jacketed reactor and the flask was rinsed into the reaction with additional dichloromethane (200 mL). The heating/cooling jacket was set to 20° C. and the reactor contents were stirred mechanically. Ethanethiol (40 mL, 540 mmol) was dissolved in 50 mL dichloromethane and added to vessel and the flask rinsed with 50 ml dichloromethane into the vessel. Boron trifluoride diethyl etherate (50 mL, 390.1 mmol) was dissolved in Stirring was set to a high speed and 4M aq. sodium acetate (1.25 L, 5100 mmol) was added. The phases were mixed well for 30 minutes. The pH of the aqueous layer was checked with a dipstick and confirmed to be ~pH=7. Stirring was turned off and the reaction mixture was left standing for 70 minutes.

The layers were separated and collected. The organic layer (bottom layer, 1.2 L) and ethanol (840 mL, 14400 mmol) were charged to the reactor. The jacket was set to 60° C. and solvent distilled under atmospheric pressure (dichloromethane bp 40° C. and ethanethiol bp 35° C., receiver flask in ice-bath). When the distillation slowed the jacket temperature was increased to 70° C. After 1300 mL of distillate were collected, a sample of the vessel content was taken and the ratio of dichloromethane to ethanol determined by $^1$H-NMR and confirmed to be under 10 mol % dichloromethane. If more dichloromethane was present further distillation would be necessary. Additional ethanol was added (400 mL) followed by seed crystals of D. The jacket was cooled to 5° C. over 30 minutes. The crystal slurry was stirred for 3 days at 5° C. The solids were collected on a sintered funnel and washed with petroleum ether (60-80° C.): 1x 500 mL slurry, 1x 300 mL plug. The solids were transferred to a 500 mL RBF and dried to constant weight (over ~4 h) on a rotary evaporator (bath temperature 45° C.) providing an off-white solid. Expected Yield: ~86 g (71% from C).

Synthesis of Compound 1

Anhydrous methanol (33 mL) was charged to a 50 mL round bottom flask. Sodium methoxide in methanol (30% solution, 25 µL, 0.135 mmol) was added and the resulting solution was stirred at ambient temperature for 5 minutes. Ethyl 3,4,6-tetra-O-acetyl-2-deoxy-2-N-phthalimido-β-thio-D-glucopyranoside (compound D) (3.09 g, 6.44 mmol) was added in portions (~200 mg) over 10 minutes, at a rate that allowed the solids to dissolve during addition. The reaction was stirred at ambient temperature for 2.5 h. TLC (EtOAc) showed complete consumption of compound D (Rf=0.9) and formation of one, more polar spot: Rf=0.5. A sample was taken and submitted for reaction completion IPC by HPLC (2.5 µL reaction mixture in 0.8 mL acetonitrile and 0.2 mL water), pass condition was NMT 1.00 area % Compound D. Acetic acid was added (8 µL, 0.1397 mmol). The pH was checked with a dipstick and confirmed to be ~pH 5-6. The mixture was concentrated on a rotary evaporator (50° C.) to near dryness. EtOAc (15 mL) was added and the majority evaporated. The residue was dissolved/slurried in 15 mL EtOAc and removed from the rotary evaporator. 2 mL petroleum ether was added and the mixture was stirred at ambient temperature. The crystal slurry was stirred overnight. The solids were collected on a sintered funnel, washed with petrol (2×10 mL) and dried on rotary evaporator (45° C. bath temperature) to constant weight. Expected Yield: 1.94 g (85% from Compound D).

Synthesis of Compound 2

Compound 1 (2.040 g) was dissolved in pyridine (28 mL) and the solution concentrated to approximately half the volume (~14 mL) in a rotary evaporator at 40° C. bath temperature to give a yellow solution. More pyridine was added (14 mL) and again the solution concentrated to approximately 14 mL in the same manner. The solution was placed under argon and trityl chloride (2.299 g, 1.36 eq) was added before an air-cooled condenser was attached and the solution heated to 50° C. with stirring. After 4 hours an IPC was run (HPLC; 5 µL into 800 µL MeCN, residual compound 1 NMT 3.00 area %). As soon as the IPC was met the reaction was cooled to 10-15° C. Benzoyl chloride (1.60 mL, 2.34 eq) was added dropwise over a period of 20 minutes keeping the reaction temperature below 20° C. Once addition was complete, the reaction was allowed to warm to ambient temperature and stirred for at least 3 h. At this time an IPC was run (HPLC; 5 µL into 1500 µL MeCN, residual mono-Bz derivatives of compound 1 NMT 3.00 area % total). As soon as the IPC was met the reaction was cooled to 0° C. and quenched by the slow addition of methanol (0.8 mL), ensuring the reaction temperature remains below 20° C. The quenched reaction was then warmed to ambient temperature.

The product mixture was diluted with toluene (20 mL) and stirred for 1 hour at ambient temperature before the precipitate was removed by filtering through a sintered funnel. The toluene solution was then washed with citric acid (20% w/w, 4×20 mL) followed by saturated NaHCO$_3$ (9% w/v, 20 mL) which resulted in a minor reaction with any residual citric acid present. The toluene (upper) layer was then washed with brine (20 mL) before being evaporated in a rotary evaporator at 40° C. bath temperature to give a yellow/orange syrup (6.833 g). The syrup was submitted for IPC (H$^1$ NMR, pass condition NMT 30 wt % residual toluene). Expected Yield: ~6.833 g (147%).

Synthesis of Compound 3

Glacial acetic acid (648 mL) and ultrapure water (72 mL) were mixed together to give a 90% acetic acid solution. A portion of the acetic acid solution (710 mL) was added to crude compound 2 (111 g) along with a stirrer bar. An air cooled condenser was attached to the flask and the mixture was then heated to 70° C. Due to the viscous nature of 2, the mixture was not fully dissolved until 1 hour and 20 minutes later, at which point stirring began. After 2 hours an IPC was run (HPLC; 5 µL into 800 µL MeCN, residual compound 2 NMT 3.00 area %). As soon as the IPC met the specs, the reaction was cooled to ambient temperature. The mixture was transferred to a sintered funnel and the precipitated trityl alcohol (31.09 g) filtered off using house vacuum. The flask was rinsed with a further portion of 90% acetic acid (40 mL) and the total washings transferred to a mixing vessel. Toluene (700 mL) and water (700 mL) were added and mixed thoroughly. The aqueous (lower) layer was a cloudy white solution and was tested for pH (it was expected to be <2). The wash was repeated twice more with water (2×700 mL; pH of ~2.4 and ~3 respectively, colorless clear solutions). Saturated NaHCO$_3$(9% w/v, 700 mL) was added to the mixing vessel resulting in a minor reaction (gas evolution). The toluene (upper) layer was then washed with brine (700 mL) before being evaporated in a rotary evaporator at 40° C. bath temperature to give a yellow/orange solid/liquid mixture (86 g). This mixture was dissolved in 400 mL toluene (300 mL+100 mL washings) and loaded on to a silica column (450 g silica) which was equilibrated with 3 column volumes (CV) of petroleum ether:toluene (1:1, v:v). The column was eluted using a stepwise gradient, fractions of 1 CV (790 mL) were collected. The gradient used was:
  4 vol % ethyl acetate in petroleum ether:toluene (1:1 v:v, 4 CVs)
  8 vol % ethyl acetate in petroleum ether:toluene (1:1 v:v, 12 CVs)
  15 vol % ethyl acetate in petroleum ether:toluene (1:1 v:v, 4 CVs)
  20 vol % ethyl acetate in petroleum ether:toluene (1:1 v:v, (4 CVs)
  30 vol % ethyl acetate in petroleum ether:toluene (1:1 v:v, 1 CV)

The product eluted over 14 fractions. TLC was used to locate the product containing fractions. All fractions were submitted to IPC (HPLC, NMT 1.50 area % of the peak at 10.14 minutes and NMT 1.50 area % of the peak at 10.94 mins). Fractions not meeting IPC were set aside for processing to compound 4. The combined fractions were evaporated in a rotary evaporator at 45° C. bath temperature to give a colorless syrup. Expected Yield: ~60 g, (78%).

Synthesis of Compound 4

Crude compound 3 (39.54 g, containing ~21 g of compound 3, ~37 mmol, taken just prior to chromatography of 3) was dissolved in toluene (7.2 mL) and dry pyridine (14.2 mL, 176 mmol, ~4.8 eq.) added to give a homogenous solution. Acetic anhydride 7.2 mL (76 mmol, ~2.1 eq.) was added and the mixture stirred for 18 h at 25° C. During the reaction solids precipitate, some of this precipitate was likely to be compound 4. The reaction was sampled for IPC, if the amount of compound 3 detected was >1.00 area % then further charges of dry pyridine (1.4 mL, 17 equivs) were added and the reaction continued until residual compound 3 was 1.00 area % in the liquid phase.

The reaction was diluted with dichloromethane (112 mL) then water (2.8 mL) and methanol (2.8 ml) were added. The mixture was stirred for 3 h at 25° C. This stir period was shown sufficient to quench the excess acetic anhydride. The mixture was washed with citric acid monohydrate/water 20/80 w/w (112 mL). The aqueous phase was back-extracted with dichloromethane (50 mL). The dichloromethane that was used for the back-extract was set aside and used to back-extract the aqueous phases from the remaining citric acid washes. The main dichloromethane extract was returned to the vessel and the citric acid washing process repeated until the pH of the aqueous phase was 2 (typically two further washes). The combined citric acid washes were back-extracted. The back-extract and main dichloromethane extract were then combined. The resulting dichloromethane solution was washed with 5% w/v NaHCO$_3$(100 mL), the dichloromethane phase was taken and washed with water (100 mL). The dichloromethane phase was transferred to an evaporating vessel and ethyl acetate (50 mL) was added and the solution concentrated to a syrup.

Ethyl acetate (150 mL) was added and the product dissolved by heating to 55° C. with stirring. Petroleum ether 60-80 (200 mL) was added and the solution re-heated to 55° C. and held for 5 min. The solution was cooled to 45° C. and seed crystals (30 mg) added, it was then cooled to 18° C. over 3 h with stirring and held at 18° C. for at least 1 h. The crystals were collected by filtration and washed with ethyl acetate/petroleum ether (1/2 v/v, 60 mL). Drying in vacuo afforded compound 4 (16.04 g, 77% from 2). Expected Yield: 16.0 g (77% from Compound 2).

Synthesis of Compound 3.1

3-aminopropan-1-ol (7.01 g, 93 mmol) was dissolved in DCM (70 mL) and cooled to 0° C. Benzyl chloroformate (5.40 mL, 32 mmol) was dissolved in DCM (20 mL) and added dropwise keeping the internal reaction temp below 10° C. Once complete, the flask was stirred at room temperature for 2 h. A sample removed for NMR analysis (IPC: 20 μL+0.6 mL d6-DMSO) indicated that the benzyl chloroformate reagent had been consumed. The product mixture was then washed with citric acid (10% w/w, 2×90 mL), water (90 mL) and brine (90 mL). The DCM (lower) layer was then evaporated in a rotary evaporator at 40° C. bath temperature to give a slightly cloudy oil/liquid (6.455 g). This oil was dissolved in ethyl acetate (7 mL), warming to 40° C. if necessary to dissolve any precipitated solid, and then allowed to cool to room temperature. Petroleum ether (4 mL) was added slowly to the stirring solution along with a seed crystal, at which point the product started crystallizing slowly. Once the majority of the product had precipitated, the final portion of petroleum ether (17 mL) was then added slowly (total solvent added: ethyl acetate:petroleum ether 1:3, 21 mL). The product was then filtered under vacuum and washed with petroleum ether (5 mL) to give the product as a fine white powder (4.72 g). Expected Yield: ~4.7 g (61%).

Synthesis of Compound 5

Compound 4 (1.05 g, 1.73 mmol) was dissolved in dry acetone (12 mL, 0.06% w/w water) and water (39 μL, 2.15 mmol, 1.3 eq.) at ambient temperature. The solution was then cooled to −10° C. NBS (0.639 g, 3.59 mmol, 2.08 eq.) was added in one portion. An exotherm in the order of +7° C. was expected and the solution was then immediately re-cooled to −10° C. 15 minutes after the NBS addition, the reaction mixture was submitted for IPC (HPLC, pass condition less than 2.00 area % compound 4 remaining). If the reaction was not complete, 1.00 eq. of NBS (0.307 g, 1.73 mmol, 1.00 eq.) was added in one portion, the reaction was then held at −10° C. for another 15 minutes and a further IPC carried out. The reaction was quenched by adding aqueous NaHCO$_3$(5% w/v, 5 mL) and cooling was stopped and the mixture allowed to warm to 10-20° C. during the following additions. After 3-5 minutes of stirring, further aqueous NaHCO$_3$(5% w/v, 5 mL) was added and stirring continued for 5 minutes. A final aliquot of aqueous NaHCO$_3$(5% w/v, 10 mL) was added with stirring followed by sodium thiosulfate (20% w/v, 5 mL). The mixture was stirred for 20 min. at 10-20° C. and the solids were then collected by filtration. The vessel was rinsed onto the filter pad with NaHCO$_3$(5% w/v, 25 mL) and this rinse was filtered off. The filter cake was then rinsed successively with NaHCO$_3$(5% w/v, 25 mL) and then water (25 mL). The (still-damp) filter cake was dissolved in DCM (20 mL) and washed with two lots of NaHCO$_3$(5% w/v, 20 mL) and then once with water (20 mL). The dichloromethane layer was dried by rotary evaporation and then dissolved in ethyl acetate (36 mL) at 65° C. Petroleum ether 60-80 (10 mL) was then added slowly with stirring and the mixture cooled to 45° C. and stirred at 45° C. for 30 min. Additional petroleum ether 60-80 (22 mL) was added with stirring and the stirred mixture cooled to 15° C. over 2 h. The product was collected by filtration, washed with petroleum ether/ethyl acetate 2/1 v/v (20 mL) and then dried under vacuum to give compound 5 (0.805 g, 83% yield, a and (3 anomers combined purity by HPLC was 98%).

Synthesis of Compound 7

Compound 4 (500 mg) and intermediate 3.1 (211 mg, 1.2 eq.) were weighed into a dry flask, toluene (5 mL) was added and the solution concentrated on a rotary evaporator (45° C. bath temperature). This was repeated once more before the starting materials were concentrated from anhydrous DCM (5 mL). Once all of the solvent was removed, the residual solid was dried under vacuum for 10 minutes. Following drying, the starting materials were placed under argon, dissolved in anhydrous DCM (5.0 mL) and activated 4 Å molecular sieves (450 mg, pellet form) were added. At this point, the NIS reagent was placed under high-vacuum to dry. After 10 minutes, the dried NIS (400 mg, 2.0 equivalents) was added and the solution stirred at room temperature for 30 minutes. TMSOTf (8 μL, 5 mol %) was then added quickly, which results in the solution changing from red/orange to a deep red/brown color. The reaction temperature also rose from 22 to 27° C. As soon as the TMSOTf was added an IPC was run for information only (HPLC; 10 μL into 1 mL MeCN—H$_2$O (8:2)). The reaction was then quenched by the addition of pyridine (20 μL, 0.245 mmol) and stirred at ambient temperature for 5 minutes. The DCM solution was filtered to remove the molecular sieves and then washed with 10% Na2S2O3 (3×5 mL), brine (5 mL) and then concentrated on a rotary evaporator (40° C. bath temperature) to give crude compound 7 as a foamy yellow oil (616 mg). Expected Yield: ~616 mg, (99%).

Synthesis of Compound 8

Crude compound 7 (16.6 g) was dried by evaporation from toluene (2×30 mL) then from anhydrous DCM (30 mL) to produce a yellow foam/oil. The flask was then placed under an argon atmosphere before anhydrous DCM (100 mL) and dry MeOH (260 mL) was added and the mixture stirred. The flask was then cooled to 0° C. Acetyl chloride (3.30 mL, 2.0 eq.) was added dropwise while maintaining an internal temp of less than 10° C. Once addition was complete, the mixture was stirred at ambient temperature for 16 hours. At this point an IPC was run (HPLC; 20 μL into 1 mL MeCN, residual compound 7 no more than 3 area %). The flask was then cooled to 0° C. and the pH of the product solution adjusted to pH 6.5-7.5 by the addition of N-methylmorpholine (7.0 mL total required). The product mixture was diluted with DCM (50 mL) and washed with $H_2O$ (2×200 mL). The second $H_2O$ wash was cloudy and contained target material by TLC so this was back-extracted with DCM (50 mL). The combined DCM layers were then washed with brine (8 mL) before being evaporated in a rotary evaporator at 40° C. bath temperature to give an off-white foam/oil (~16.8 g). This mixture was dissolved in 140 mL toluene (100 mL+40 mL washings) and loaded onto a silica column (85 g silica) which was equilibrated with 3 column volumes (CV) of 30 vol % ethyl acetate in petroleum ether. The column was eluted using a stepwise gradient, fractions of 1 CV (140 mL) were collected. The gradient used was:
- 30 vol % ethyl acetate in petroleum ether (3 CVs)
- 35 vol % ethyl acetate in petroleum ether (4 CVs)
- 40 vol % ethyl acetate in petroleum ether (9 CVs)
- 50 vol % ethyl acetate in petroleum ether (4 CVs)
- 60 vol % ethyl acetate in petroleum ether (3 CVs)
- The product eluted over 12 fractions. All fractions were submitted to IPC (HPLC, NMT 1.50 area % of any impurity peak at 230 nm). The combined fractions were evaporated in a rotary evaporator at 40° C. bath temperature to give an off-white foam which solidified to afford 8 as a crunchy solid (10.45 g). Expected Yield: 10.45 g (66%).

Example 4—Synthesis of Disulfide (Compound 17)

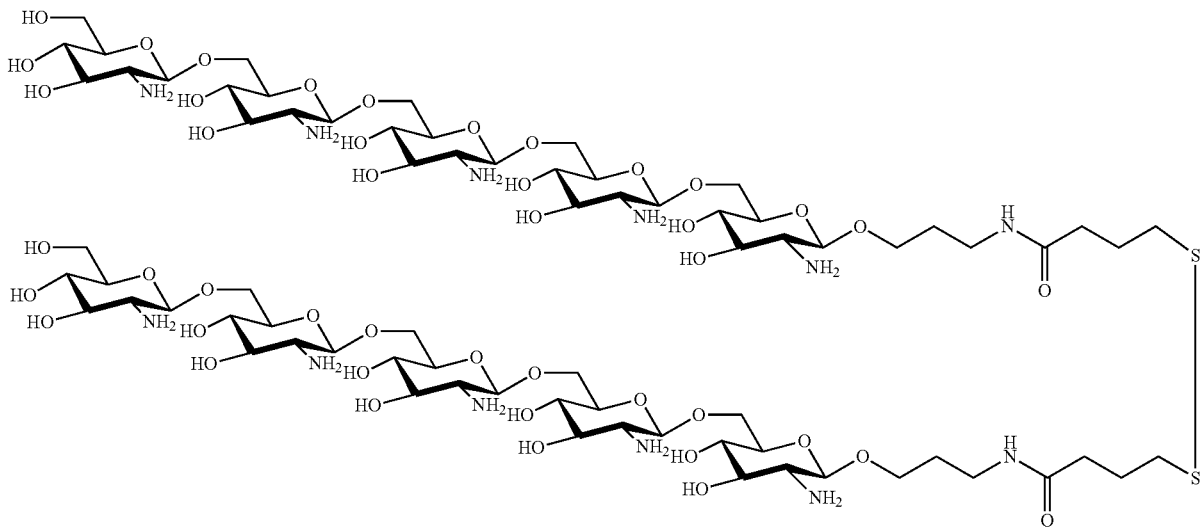

Compound 17

The overall synthetic procedure for the synthesis of compound 17 is described in the synthetic scheme below.

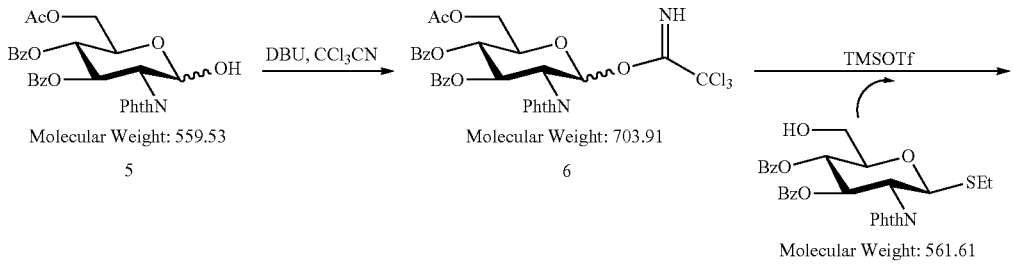

-continued
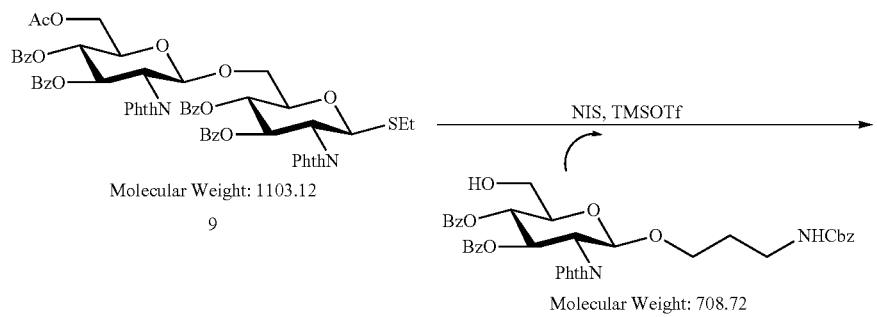
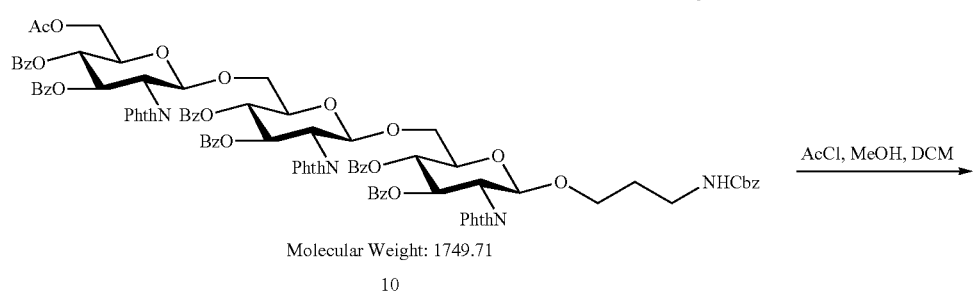
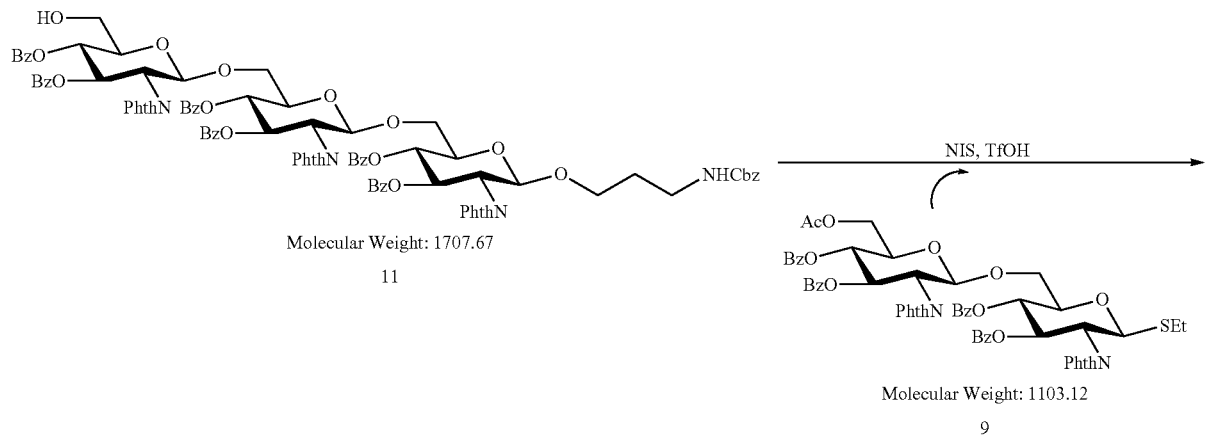
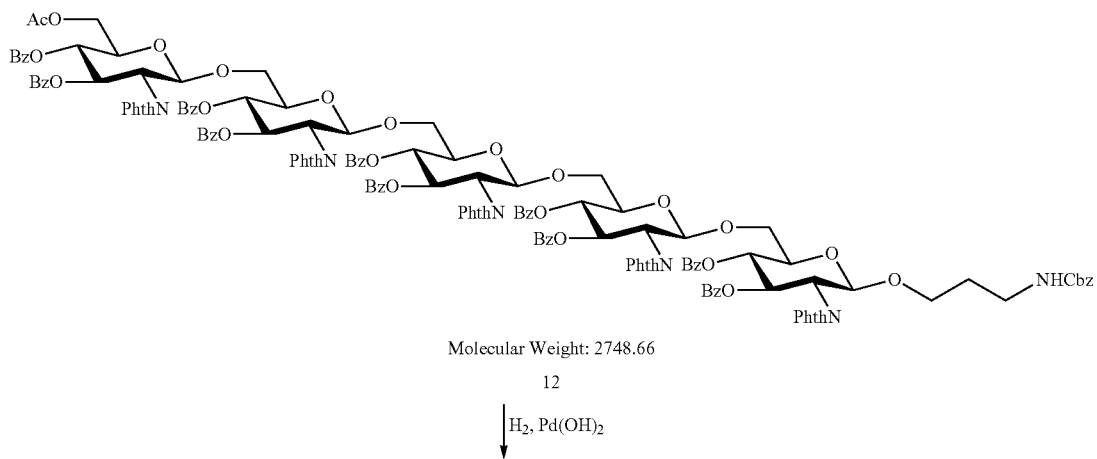

-continued

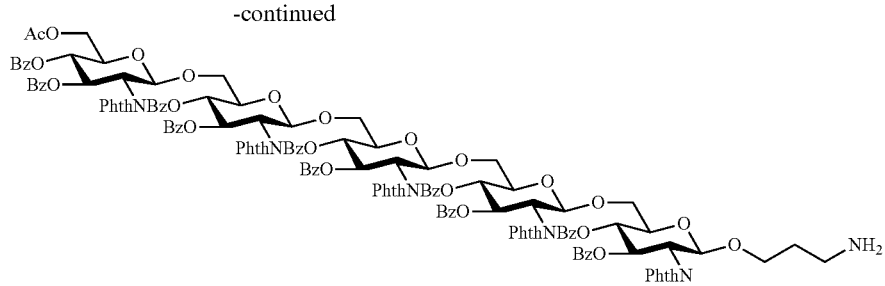

Molecular Weight: 2614.52

13

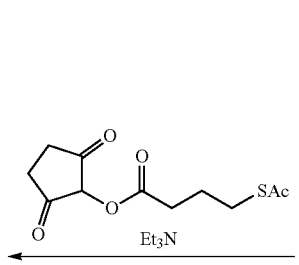

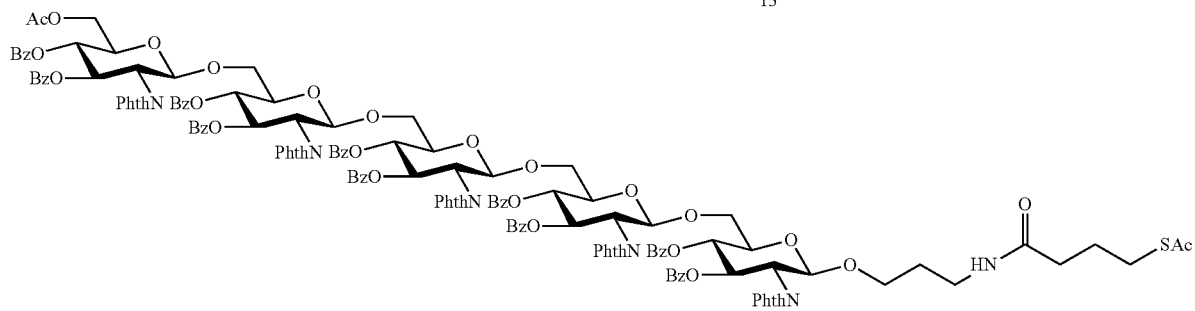

Molecular Weight: 2758.71

16

$$\Big| N_2H_4\text{—}H_2O, EtOH$$
Reflux, 1 hr

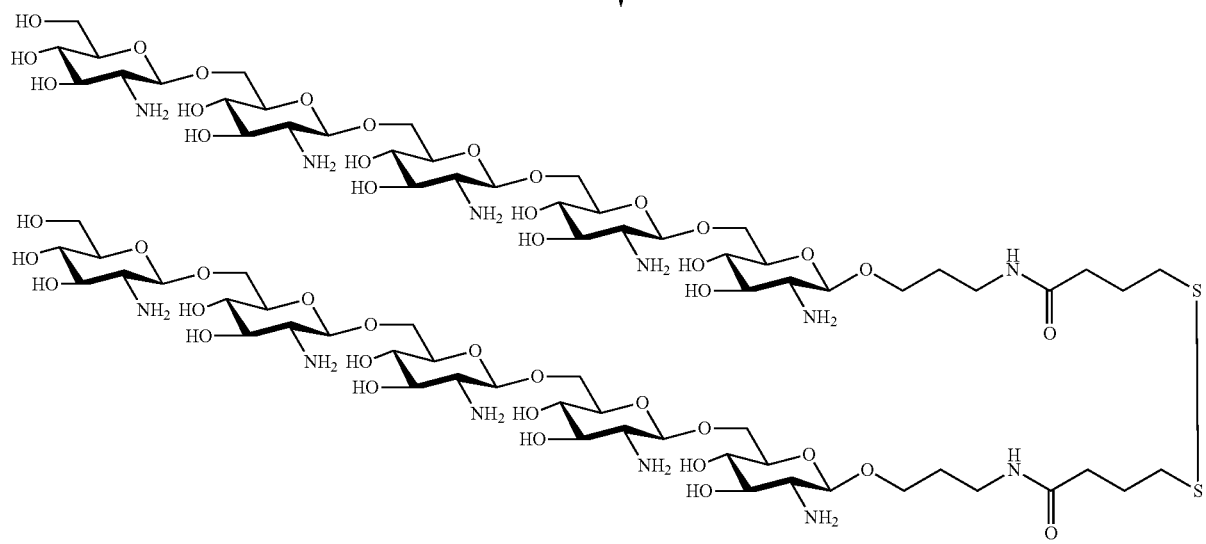

Molecular Weight: 1964.08

17

Synthesis of Compound 9

Compound 5 (1620 g, 1.18 eq.) and toluene (18 kg) were charged to a 50 L Büchi bowl in that order. The bowl was warmed in a water bath with a setting of 50±10° C. for 30 min. Evaporation was run under vacuum using a water bath temperature of 50±10° C. until no more solvent distilled. The water bath was cooled to 20±10° C. Trichloroacetonitrile (7.1 kg, 21 equiv.) and dry DCM (6.5 kg) were charged to the bowl under nitrogen atmosphere. A suspension of sodium hydride (5.6 g, 0.060 equiv.) in dry DCM (250 g) was charged to the bowl under nitrogen atmosphere. The bowl contents were mixed by rotation for 1-2 h with a water bath temperature of 20±10° C. Compound 5 dissolved during the reaction. The bowl contents were sampled and submitted for reaction completion IPC (H$^1$ NMR, integrating triplet peak at 6.42 ppm (product) relative to triplet at 6.35 ppm (starting material); pass condition 5% residual starting material). Compound 3 (1360 g, 2.35 mol), dry DCM (12.3 kg) and powdered molecular sieves 4 Å (136 g) were charged to the 50 L reactor in that order. The reactor contents were mixed for 24 h. The reactor contents were sampled through a syringe filter and analyzed by Karl Fisher (AM-GEN-011, pass condition 0.03% w/w). After reaching the moisture threshold (~24 h), the reactor contents were adjusted to 0±5° C. The contents of the Büchi bowl were transferred to the reactor header as volume allowed. A solution of trimethylsilyl trifluoromethanesulfonate (100 g, 0.18 eq.) in dry DCM (1250 g) was charged to the reactor under a nitrogen atmosphere. The header contents were drained to the reactor maintaining the reactor contents at 0±10° C. throughout the addition. Addition took 15-20 min. Dry DCM (1250 g) was charged to the Büchi bowl and then transferred to the reactor header. The header contents were drained to the reactor maintaining the reactor contents at 0±10° C. throughout the addition. The reactor contents were stirred at 0±5° C. for 60 min. The reactor contents were sampled for reaction completion using IPC (HPLC, pass criteria 5% starting material). The reaction was quenched by charging N-methylmorpholine (85 g, 0.36 eq.) to the reactor. The reactor contents were sampled for quench completion using IPC (wetted pH paper, pass criteria≥pH 7). Silica gel (4.9 kg) was charged to the Büchi bowl. The reactor contents were transferred to the Büchi bowl. Evaporation was run under vacuum using a water bath temperature of 40±10° C. until no more solvent distilled. Silica gel (1.4 kg) was charged to the Büchi bowl followed by dichloromethane (7.0 kg) used to rinse the reactor. The bowl contents were rotated to ensure solids were not adhered to the bowl surface. Evaporation was run under vacuum using a water bath temperature of 40±10° C. until no more solvent distilled. The bowl contents were divided into three portions for silica gel chromatography. A 150 L KP-SIL cartridge was installed in the Biotage system. Ethyl acetate (7.8 kg) and petroleum ether (22 kg) were charged to the 50 L reactor along with 1/3 of the reaction mixture adsorbed onto silica gel, mixed thoroughly and then transferred to a Biotage solvent reservoir. The solvent reservoir contents were eluted through the column so as to condition the column. The eluent was collected in 20 L jerry cans and discarded. The column was run in three batches and each was eluted with ethyl acetate/petroleum ether as described below:

Ethyl acetate (1.6 kg) and Petroleum ether (4.4 kg) were charged to a Biotage solvent reservoir, mixed thoroughly and then eluted through the column. Column run-off was collected in 20 L jerry cans.

Ethyl acetate (25 kg) and Petroleum ether (26 kg) were charged to the 50 L reactor, mixed thoroughly, transferred to two Biotage solvent reservoirs and then eluted through the column. Column run-off was collected in 20 L jerry cans.

Ethyl acetate (31 kg) and Petroleum ether (22 kg) were charged to the 50 L reactor, mixed thoroughly, transferred to two Biotage solvent reservoirs and then eluted through the column. Column run-off was collected in 5 L glass lab bottles.

Ethyl acetate (16 kg) was charged to a Biotage solvent reservoir and then eluted through the column. Column run-off was collected in 20 L jerry cans.

The column was repeated as above with the remaining two portions of dry load silica prepared.

The column fractions were sampled for product purity (TLC [10% acetone in toluene, Rf 0.5] to identify fractions with product. The accepted column fractions were combined and in a 100 L Büchi bowl. Toluene was used to rinse any crystalline material from accepted fraction vessels into the bowl. Evaporation was run under vacuum using a water bath temperature of 40±10° C. until no more solvent distilled. Toluene (1.7 kg) was charged to the bowl and to contents rotated until the solids dissolved. t-Butyl methyl ether (4.4 kg) was charged to the bowl over 20-40 min. The bowl contents were rotated for 12-24 h at a temperature of 20±5° C. The bowl contents were transferred to a 6 L Nutsche filter and the solvent removed by vacuum filtration. t-Butyl methyl ether (620 g) was charged to the bowl, transferred to the Nutsche filter and passed through the filter cake. The filter cake was air dried in the filter then transferred to a vacuum oven and dried at a setting of 30° C. under vacuum to remove residual solvent. The solid was sampled for analytical and retention. The solid was transferred to screw-top Nalgene containers and stored at ° C. Expected Yield: 1.68-1.94 kg compound 9 (65-75%).

Synthesis of Compound 10

Reagents were prepared as follows: N-Iodosuccinimide (241 g, 2.20 eq.) was dried in a vacuum oven with a setting of 30° C. under vacuum for 24 h. A solution of sodium chloride (300 g) in water (3000 g) was prepared in a 5 L lab bottle. A solution of sodium thiosulfate (1100 g) in water (6000 g) was prepared in a 50 L reactor and distributed into two portions.

Compound 8 (355 g, 0.486 mol) and Compound 9 (634 g, 1.10 eq.) were charged to a 20 L Büchi bowl followed by toluene (1500 g) and heated at 40±5° C. until dissolved. Evaporation was run under vacuum using a water bath temperature of 35±10° C. until no more solvent distilled. Toluene (1500 g) was charged to the Büchi bowl. Evaporation was run under vacuum using a water bath temperature of 35±10° C. until no more solvent distilled. Dry dichloromethane (4000 g) was charged to the Büchi bowl. The bowl was rotated until the solids dissolved and the solution was transferred to a 5 L reactor with a jacket temperature of 20° C.±5° C. Dry dichloromethane (710 g) was charged to the Büchi bowl. The bowl was rotated to rinse the bowl surface and the solution was transferred to the 5 L reactor. The reactor contents were sampled for reagent ratio IPC ($H^1$ NMR). Dried N-Iodosuccinimide was charged to the reactor under a nitrogen atmosphere and the reactor was stirred for 5-15 min. The reactor contents were adjusted to 20° C.±3° C. Trimethylsilyl trifluoromethanesulfonate (5.94 g, 0.055 eq.) in dry DCM (60 g) was charged to the reactor over 5-15 min. maintaining the contents temperature at 20° C.±3° C. The reaction mixture was stirred at 20° C.±3° C. for 20±3 min. The reactor contents were sampled for reaction completion (HPLC). N-Methylmorpholine (98 g, 2 equiv.) was charged to the reactor and mixed thoroughly. One of the portions of the sodium thiosulfate solution prepared above was charged to the 50 L reactor. The κL reactor contents were transferred to the 50 L reactor containing the sodium thiosulfate solution and mixed thoroughly. The bottom layer was discharged to a HDPE jerry can.

DCM (570 g) was charged to the 5 L reactor with the top layer from the 50 L reactor and mixed thoroughly. The bottom layer was combined with the previous bottom layer in the HDPE jerry can. The top layer was transferred to a separate HDPE jerry can and retained until yield was confirmed. The combined organic phase (bottom layers) were charged to the 50 L reactor followed by another portion of sodium thiosulfate and mixed thoroughly. The bottom layer was discharged to a HDPE jerry can. The top layer was retained in a HDPE jerry can until yield was confirmed. The sodium chloride solution was charged to the 50 L reactor along with the organic phase (bottom layers) and mixed thoroughly. Silica gel (1300 g) was charged to a Büchi bowl and fitted with a rotary evaporator. The bottom layer in the reactor was charged to the Büchi bowl. The bowl contents were rotated to prevent adsorption onto the bowl and evaporated under vacuum using a water bath temperature of 40±5° C. until no more solids distilled. The bowl contents were divided into two equal portions. Silica gel (200 g) was charged to the Büchi bowl followed by dichloromethane (700 g). The bowl contents were rotated to ensure solids did not adhere to the bowl surface. The bowl was evaporated under vacuum at a water bath temperature of 40° C.±10° C. until no more solvent distilled. The bowl contents were divided into two portions and a portion was added to each of the previous silica gel samples.

Each portion was purified independently on silica gel using the following procedure (samples were stored at 15° C. while awaiting purification): A 150 L KP-SIL cartridge was installed in the Biotage system. Ethyl acetate (15.5 kg) and petroleum ether (16.5 kg) were charged to the 50 L reactor, mixed thoroughly and then transferred to two Biotage solvent reservoirs. The solvent reservoirs contents were eluted through the column so as to condition the column. The eluent was collected in 20 L jerry cans and discarded. A portion of the dry load silica from above was charged to the Biotage Sample-Injection Module (SIM) and then eluted with the ethyl acetate/petroleum ether as follows:

Ethyl acetate (6.2 kg) and Petroleum ether (6.6 kg) were charged to a 50 L reactor, mixed thoroughly and then transferred to a Biotage solvent reservoir. Column run-off was collected in 20 L jerry cans.

Ethyl acetate (19.5 kg) and Petroleum ether (19.2 kg) were charged to the 50 L reactor, mixed thoroughly, transferred to two Biotage solvent reservoirs and then eluted through the column. Column run-off was collected in 20 L jerry cans.

Ethyl acetate (13.6 kg) and Petroleum ether (12.3 kg) were charged to the 50 L reactor, mixed thoroughly, transferred to two Biotage solvent reservoirs and then eluted through the column. Column run-off was collected in 20 L jerry cans.

Ethyl acetate (14.2 kg) and Petroleum ether (11.9 kg) were charged to the 50 L reactor, mixed thoroughly, transferred to two Biotage solvent reservoirs and then eluted through the column. Column run-off was collected in 20 L jerry cans.

Ethyl acetate (29.7 kg) and Petroleum ether (22.9 kg) was charged to a Biotage solvent reservoir and then eluted through the column. Column run-off was collected in 20 L jerry cans up to fraction 11 and then 5 L HDPE jerry cans.

Ethyl acetate (15.5 kg) and Petroleum ether (11.0 kg) was charged to a Biotage solvent reservoir and then eluted through the column. Column run-off was collected in 5 L HDPE jerry cans.

Ethyl acetate (29.7 kg) and Petroleum ether (13.2 kg) was charged to a Biotage solvent reservoir and then eluted through the column. Column run-off was collected in 5 L HDPE jerry cans.

Ethyl acetate (15.5 kg) was charged to a Biotage solvent reservoir and then eluted through the column. Column run-off was collected in 5 L HDPE jerry cans.

Column fractions were sampled for product purity (TLC to identify fractions with product). Fractions that were 75-95% area compound 10 from the first two columns were combined in a Büchi bowl charged with silica gel (400 g) and evaporation was run under vacuum using a water bath temperature of 40±10° C. until no more solvent distilled. The contents of the bowl were purified as follows: A 150 L KP-SIL cartridge was installed in the Biotage system. Ethyl acetate (15.5 kg) and petroleum ether (16.5 kg) were charged to the 50 L reactor, mixed thoroughly and then transferred to two Biotage solvent reservoirs. The solvent reservoirs contents were eluted through the column so as to condition the column. The eluent was collected in 20 L jerry cans and discarded. The bowl contents were charged to the Biotage Sample-Injection Module (SIM) and then eluted with the ethyl acetate/petroleum ether as follows:

Ethyl acetate (6.2 kg) and Petroleum ether (6.6 kg) were charged to a 50 L reactor, mixed thoroughly and then transferred to a Biotage solvent reservoir. Column run-off was collected in 20 L jerry cans.

Ethyl acetate (19.5 kg) and Petroleum ether (19.2 kg) were charged to the 50 L reactor, mixed thoroughly, transferred to two Biotage solvent reservoirs and then eluted through the column. Column run-off was collected in 20 L jerry cans.

Ethyl acetate (13.6 kg) and Petroleum ether (12.3 kg) were charged to the 50 L reactor, mixed thoroughly, transferred to two Biotage solvent reservoirs and then eluted through the column. Column run-off was collected in 20 L jerry cans.

Ethyl acetate (14.2 kg) and Petroleum ether (11.9 kg) were charged to the 50 L reactor, mixed thoroughly, transferred to two Biotage solvent reservoirs and then eluted through the column. Column run-off was collected in 20 L jerry cans.

Ethyl acetate (29.7 kg) and Petroleum ether (22.9 kg) was charged to a Biotage solvent reservoir and then eluted through the column. Column run-off was collected in 20 L jerry cans up to fraction 11 and then 5 L HDPE jerry cans.

Ethyl acetate (15.5 kg) and Petroleum ether (11.0 kg) was charged to a Biotage solvent reservoir and then eluted through the column. Column run-off was collected in 5 L HDPE jerry cans.

Ethyl acetate (29.7 kg) and Petroleum ether (13.2 kg) was charged to a Biotage solvent reservoir and then eluted through the column. Column run-off was collected in 5 L HDPE jerry cans.

Ethyl acetate (15.5 kg) was charged to a Biotage solvent reservoir and then eluted through the column. Column run-off was collected in 5 L HDPE jerry cans.

The accepted column fractions from all three columns were combined in a Büchi bowl and evaporation was run under vacuum using a water bath with temperature of 40° C.±10° C. until no more solvent distilled. The contents of the bowl were sampled for analytical and retention. The bowl was sealed and transferred to storage at ≤−15° C. Expected Yield: 440-540 kg (52-64% yield).

Synthesis of Compound 11

Dichloromethane was charged to a Büchi bowl containing compound 10 (635 g, 0.345 mol) (PN0699) and heated at 30±10° C. until dissolved. Methanol (3.2 kg) was charged to the bowl. The content of the bowl were adjusted to 0±3° C. Acetyl chloride (54.1 g, 2 equiv.) in dichloromethane (660 g) was charged to the bowl maintaining the contents temperature at 0±10° C. The bowl contents were adjusted to 20±3° C. and the mixture was stirred for 40-48 h. The bowl contents were sampled for reaction completion IPC (HPLC, pass). The bowl contents were adjusted to 0±3° C. N-methylmorpholine (139 g, 4 equiv.) was charged to the bowl and mixed thoroughly. The bowl contents were sampled for quench completion IPC (pH paper, pass≤pH7). The bowl contents were concentrated under vacuum with water bath at 35±10° C. Ethyl acetate (4.8 kg) and water (5.5 kg) were charged to the Büchi bowl and rotated to dissolve the bowl contents. The bowl contents were transferred to a 50 L reactor and mixed thoroughly. The bottom layer was drained to a HDPE jerry can. The top layer was transferred to a Büchi bowl fitted with a rotary evaporator and the contents were concentrated under vacuum with a water bath at 35±10° C. The bottom layer from the HDPE jerry can was charged to a 50 L reactor with ethyl acetate (1.5 kg) and mixed thoroughly. The bottom layer was drained to a HDPE jerry can and held until yield was confirmed. The top layer was transferred to the Büchi bowl fitted with a rotary evaporator and the contents were concentrated under vacuum with a water bath at 35±10° C. The contents of the bowl were sampled for analytical and retention. The bowl was sealed and transferred to storage at −15° C. Expected Yield: 518-633 kg (90-110% yield).

Synthesis of Compound 12

Reagents were prepared as follows: Two portions of N-Iodosuccinimide (143 g, 3.90 eq.) were dried in a vacuum oven with a setting of 30° C. under vacuum for 24 h. A solution of sodium chloride (450 g) in water (1850 g) was prepared in a 5 L lab bottle and distributed to 2 approximately equal portions. A solution of sodium thiosulfate (230 g) in water (2080 g) was prepared in a 5 L lab bottle and distributed to 4 approximately equal portions.

Compound 9 (504 g, 1.30 eq.) was charged to a 50 L Büchi bowl containing compound 11 (607 g, 0.327 mol) followed by toluene (1500 g) and heated at 40±5° C. until dissolved. Evaporation was run under vacuum using a water bath temperature of 35±10° C. until no more solvent distilled. Toluene (1500 g) was charged to the Büchi bowl. Evaporation was run under vacuum using a water bath temperature of 35±10° C. until no more solvent distilled. Dry DCM (2400 g) was charged to the Büchi bowl. The bowl was rotated until the solids dissolved and half the solution transferred to the 5 L reactor with a jacket temperature of 20° C.±5° C. The second half of the solution was transferred to a 5 L lab bottle. Dry DCM (710 g) was charged to the Büchi bowl. The bowl was rotated to rinse the bowl surface and half the solution was transferred to the 5 L reactor. The other half was charged to the 5 L lab bottle above and stored under nitrogen for use in the second batch. A portion of dried N-Iodosuccinimide was charged to the reactor under a nitrogen atmosphere. The reactor contents were adjusted to −40° C.±3° C. Trimethylsilyl trifluoromethanesulfonate (9.09 g, 0.25 effective equiv.) in dry dichloromethane (90 g) was charged to the reactor over 15 min. maintaining the contents temperature at −40° C.±5° C. The reaction mixture was stirred at −40° C.±3° C. for 30±5 min. then adjusted to −30° C.±3° C. over and stirred for 150 min. The reactor contents were sampled for reaction completion. N-Methylmorpholine (33.1 g, 2 effective eq.) was charged to the reactor and mixed thoroughly. One of the portions of the sodium thiosulfate solution prepared above was charged to the 5 L reactor and mixed thoroughly. The bottom layer was discharged to a 5 L lab bottle. DCM (400 g) was charged to the 5 L reactor and mixed thoroughly. The bottom layer was combined with the previous bottom layer in a 5 L lab bottle. The combined organic phases were charged to the 5 L reactor followed by another portion of sodium thiosulfate and mixed thoroughly. The bottom layer was discharged to a 5 L lab bottle. A portion of sodium chloride solution from above was charged to the reactor followed by the content of the previous lab bottle. The bottom layer in the reactor was charged to the Büchi and evaporated under vacuum using a water bath temperature of 40±10° C. until no more solvent distilled. The reactor was cleaned and dried.

The second portion of compound 9 and compound 11 were charged to the reactor and treated identically to first batch. Following organic extraction of the second batch, the reaction mixtures were combined in the reactor. A portion of sodium chloride solution was charged to the reactor and mixed thoroughly. Silica gel (1700 g) was charged to a Büchi bowl and fitted to a rotavapor. The bottom layer in the reactor was charged to the Büchi and evaporated under vacuum using a water bath temperature of 40±10° C. until no more solvent distilled. The bowl contents were divided into two portions purified independently on silica gel. A 150 L KP-SIL cartridge was installed in the Biotage system (commercially available from Biotage, a division of Dyax Corporation, Charlottesville, Va., USA). Ethyl acetate (7.7 kg) and petroleum ether (22.0 kg) were charged to the 50 L reactor, mixed thoroughly and then transferred to two Biotage solvent reservoirs. The solvent reservoirs contents were eluted through the column so as to condition the column. The eluent was collected in 20 L jerry cans and discarded. A portion of the dry load silica from above was charged to the Biotage Sample-Injection Module (SIM) and then eluted with the ethyl acetate/petroleum ether as follows:

Ethyl acetate (1.5 kg) and Petroleum ether (4.4 kg) were charged to a HDPE jerry can, mixed thoroughly and then transferred to a Biotage solvent reservoir. Column run-off was collected in 20 L jerry cans.

Ethyl acetate (18.6 kg) and Petroleum ether (8.8 kg) were charged to the 50 L reactor, mixed thoroughly, transferred to two Biotage solvent reservoirs and then eluted through the column. Column run-off was collected in 20 L jerry cans.

Ethyl acetate (19.2 kg) and Petroleum ether (8.4 kg) were charged to the 50 L reactor, mixed thoroughly, transferred to two Biotage solvent reservoirs and then eluted through the column. Column run-off was collected in 20 L jerry cans.

Ethyl acetate (29.7 kg) and Petroleum ether (11.9 kg) were charged to the 50 L reactor, mixed thoroughly, transferred to two Biotage solvent reservoirs and then eluted through the column. Column run-off was collected in 20 L jerry cans.

Ethyl acetate (15.5 kg) was charged to a Biotage solvent reservoir and then eluted through the column. Column run-off was collected in 5 L glass lab bottles.

Column fractions were sampled for product purity (TLC to identify fractions with product). Fractions that were 75-95% area compound 12 from the first two columns were combined in a Büchi bowl charged with silica gel (400 g) and evaporation was run under vacuum using a water bath temperature of 40±10° C. until no more solvent distilled. Ethyl acetate (7.7 kg) and petroleum ether (22.0 kg) were charged to the 50 L reactor, mixed thoroughly and then transferred to two Biotage solvent reservoirs. The solvent reservoirs contents were eluted through the column so as to condition the column. The eluent was collected in 20 L jerry cans and discarded. The dry load silica containing the impure product was charged to the Biotage Sample-Injection Module (SIM) and then eluted as detailed below:

Ethyl acetate (1.5 kg) and Petroleum ether (4.4 kg) were charged to the 50 L reactor, mixed thoroughly and then transferred to a Biotage solvent reservoir. Column run-off was collected in 20 L jerry cans.

Ethyl acetate (19.2 kg) and Petroleum ether (8.4 kg) were charged to the 50 L reactor, mixed thoroughly, transferred to two Biotage solvent reservoirs and then eluted through the column. Column run-off was collected in 20 L jerry cans.

Ethyl acetate (18.6 kg) and Petroleum ether (8.8 kg) were charged to the 50 L reactor, mixed thoroughly, transferred to two Biotage solvent reservoirs and then eluted through the column. Column run-off was collected in 20 L jerry cans.

Ethyl acetate (29.7 kg) and Petroleum ether (11.9 kg) were charged to the 50 L reactor, mixed thoroughly, transferred to two Biotage solvent reservoirs and then eluted through the column. Column run-off was collected in 20 L jerry cans.

Ethyl acetate (15.5 kg) was charged to a Biotage solvent reservoir and then eluted through the column. Column run-off was collected in 5 L glass lab bottles.

Column fractions were sampled for product purity (TLC to identify fractions with product, HPLC pass criteria ≥95% compound 12 and no single impurity>2.5%). The accepted column fraction from all three columns were combined in a Büchi bowl and evaporation was run under vacuum using a water bath temperature of 40±10° C. until no more solvent distilled. The contents of the bowl was sampled for analytical and retention. Bowl was sealed and transferred to storage at ≤−15° C. Expected Yield: 494-584 kg (52-64% yield).

Synthesis of Compound 13

Glacial acetic acid (7.5 kg) and ethyl acetate (6.5 kg) were combined in a suitable container and labeled as "GAA/EA solution". Sodium bicarbonate (0.5 kg) was dissolved in RO water (10 kg) and labelled as "5% w/w sodium bicarbonate solution." Palladium on activated carbon (100 g, specifically Johnson Matthey, Aliso Viejo, Calif., USA, Product No. A402028-10) and GAA/EA solution (335 g) was charged into a reaction vessel in that order. Compound 12 (270 g) was dissolved in GAA/EA solution (1840 g) and transferred to a 50 L reaction vessel. The solution was purged of oxygen by pressurization with nitrogen to 10 bar and then released. This was repeated twice more. The reactor contents were pressurized under hydrogen to 10 bar and then released. The reaction mixture was hydrogenated at 20 bar $H_2$ for 1.5 days. The pressure was then released and the solution purged of hydrogen by pressurization with nitrogen to 10 bar and then release. This was repeated once. Reaction mixture was filtered through a pad of Celite (300 g). The celite cake was washed with GAA/EA solution (2×5.5 kg). Filtrates were combined and evaporated under vacuum (bath temperature 40±5° C.). The residue was co-evaporated with ethyl acetate (2.3 kg) in two portions. The expected weight of the crude product was ~316 g. A Biotage system was equipped with 150 M KP-SIL cartridge with a 5 L Sample Injection Module (SIM). Ethyl acetate (10.6 kg) and glacial acetic acid (1.4 kg) were charged to the 50 L reactor, mixed thoroughly and then transferred to a Biotage solvent reservoir. The contents of the solvent reservoir were eluted through the column so as to condition the column. The eluent was discarded. The crude product was dissolved in ethyl acetate (422 g) and glacial acetic acid (55 g). The resulting solutions were charged to the SIM and passed onto the column. The reaction mixture was chromatographed as follows:

Ethyl acetate (13.8 kg) and glacial acetic acid (1.8 kg) were charged to the 50 L reactor, mixed thoroughly and then transferred to a Biotage solvent reservoir.

The contents of the solvent reservoir were eluted through the SIM onto the column and the eluent was collected in a 20 L jerry can.

Ethyl acetate (10.3 kg), glacial acetic acid (1.3 kg) and methanol (206 g) were charged to the 50 L reactor, mixed thoroughly and then transferred to a Biotage solvent reservoir.

The contents of the solvent reservoir were eluted through the column and the eluent was collected in a 5 L jerry cans.

Ethyl acetate (6.6 kg), glacial acetic acid (0.9 kg) and methanol (340 g) were charged to the 50 L reactor, mixed thoroughly and then transferred to a Biotage solvent reservoir.

The contents of the solvent reservoir were eluted through the column and the eluent was collected in ~2.5 L fractions in 5 L jerry cans.

Ethyl acetate (31.4 kg), glacial acetic acid (4.1 kg) and methanol (3.4 kg) were charged to the 50 L reactor, mixed thoroughly and then transferred to a Biotage solvent reservoir.

The contents of the solvent reservoir were eluted through the column and the eluent was collected in 5 L jerry cans.

Fractions containing compound 13 were combined and evaporated under vacuum (bath temperature 40±5° C.). Residue was dissolved in ethyl acetate (3.1 kg) and washed with 5% w/w sodium bicarbonate solution (9.3 kg), ensuring the pH of the aqueous medium was 8. The ethyl acetate phase was evaporated under vacuum (bath temperature 40±5° C.). The contents of the bowl was sampled for analytical and retention. Expected Yield: 182-207 g (71-81%).

Synthesis of Compound 16

Dry dichloromethane (2.5 kg) was charged to a Büchi bowl containing compound 13 (211 g, 76.5 mmol, 1.00 eq.) and rotated without heating until dissolved. A solution of (2,5-dioxopyrrolidin-1-yl) 4-acetylsulfanylbutanoate (25.8 g, 99.4 mmol, 1.30 equiv) in dry dichloromethane (200 g) was added to the Büchi bowl. The bowl was rotated for 1 hr at ambient temperature followed by concentration under vacuum with a water bath temperature of 40±5° C. Toluene (0.8 kg) was added to the bowl and removed under vacuum with a water bath temperature of 40±5° C. twice. Toluene (0.8 kg) was added to the residue to dissolve. Silica gel (557 g) was loaded into the reaction vessel and solvents were removed under vacuum with a water bath temperature of 40±5° C. A Biotage system was equipped with a 150 M KP-SIL cartridge with a 5 L Sample Injection Module (SIM). Toluene (10.1 kg) and acetone (1.0 kg) were charged to the 50 L reactor, mixed thoroughly and then transferred to a Biotage solvent reservoir (Solvent A). The reaction mixture was purified as follows:

Solvent A was eluted through the column so as to condition the column. The eluent was discarded.

Dry loaded silica gel was transferred to the SIM.

Toluene (9.6 kg) and acetone (1.5 kg) were charged to the 50 L reactor, mixed thoroughly and then transferred to a Biotage solvent reservoir (Solvent B).

Solvent B was eluted through the column and the eluent was collected in 5 L jerry cans.

Toluene (53.6 kg) and acetone (12.2 kg) were charged to the 50 L reactor, mixed thoroughly and then transferred to Biotage solvent reservoirs (Solvent C).

Solvent C was eluted through the column and the eluent is collected in 5 L jerry cans.

Toluene (8.4 kg) and acetone (2.6 kg) were charged to the 50 L reactor, mixed thoroughly and then transferred to a Biotage solvent reservoir (Solvent D).

Solvent D was eluted through the column and the eluent was collected in a 5 L jerry cans.

Toluene (23.4 kg) and acetone (9.2 kg) were charged to the 50 L reactor, mixed thoroughly and then transferred to a Biotage solvent reservoir (Solvent E).

Solvent E was eluted through the column and the eluent was collected in a 5 L jerry cans.

Fractions containing compound 16 (pass criteria ≥90% compound 16 and no single impurity>2.5%) were combined and evaporated under vacuum (bath temperature 40±5° C.). The residue was dissolved in tetrahydrofuran (4.4 kg) and concentrated under vacuum with a water bath temperature of 40±5° C. The contents of the bowl were sampled for analytical and retention. Expected Yield: 169-192 g (76-86%).

Synthesis of Compound 17

The reactor was marked at the 2.5 L, 3.5 L and 3.9 L levels before starting and fit with a vacuum controller. Dichloromethane was charged to a Büchi Bowl containing 140 g of compound 16 and transferred to the Reactor Ready vessel. Two rinses of DCM (333 g) were used to transfer the contents of the Büchi bowl into the Reactor Ready vessel. Ethanol (2.50 kg) was added to the reactor ready. The reaction mixture was concentrated to the 2.5 L mark (target vacuum 250 mbar). Ethanol (1.58 kg) was added to the reactor ready and concentrated to the 3.5 L mark. The reaction was diluted to the 3.9 L mark with ethanol. Reactor contents were placed under inert gas by applying a partial vacuum and releasing with nitrogen. A slow flow of nitrogen was maintained during the reaction. Hydrazine monohydrate (1.13 kg, 1.11 L) was charged to the 5 L Reactor Ready vessel under a nitrogen atmosphere. The temperature ramp was set to: initial temp 20° C., final temp 60° C., with a linear temperature ramp over 50 min (0.8 deg/min) and active control on the contents of the reactor. The vessel temperature was held at 60° C. for 45 min. The cooling ramp temperature was set to: −2 deg/min, with the final temp 20° C. The contents were discharged to suitable HDPE jugs and weights determined. Equal amounts were transferred to 8 polypropylene centrifuge containers with FEP encapsulated seals. Each centrifuge container was charged with ethanol (750 g) and agitated for 30 min at ambient. The containers were centrifuged (5300 RCF, 15° C., 30 min). Residual hydrazine on the outside of the containers was removed by rinsing the outside of the bottles with acetone then water before taking out of fume hood. The supernatant in the centrifuge containers was decanted and the residual pellet was dissolved in Low Endotoxin water (LE water) (1960 g) and transferred to a 5 L Reactor Ready vessel. The contents were agitated at medium speed while bubbling air through the solution using a dispersion tube approximately 15-20 min for every 1.5 hrs. The reaction was then stirred overnight at 20° C. in a closed vessel. Once IPC indicated free pentamer composition was below 3% (area % of the total reported) the reaction was considered complete. Filtration (using a P3 sintered glass funnel and 5 L Buchner flask) was required if there were any insoluble material present in reaction mixture. Contents of the reactor were freeze-dried in 2 Lyoguard trays. The shelf temperature was set at −0.5° C. for 16-20 h and then at 20° C. until dry. Freeze-dried product was dissolved in LE water (840 g) and divide equally between 6 centrifuge bottles. Acetone (630 g) was added to each container agitated for 15 minutes. Isopropanol (630 g per container) was added to each container and agitation continued for 20 min. Contents were centrifuged at 5300 RCF at 15° C., for 1 h. The supernatants were discarded and each pellet was dissolved in water by adding LE water (140 g) to each container and then agitating the mixture at ambient using an orbital shaker until the pellets dissolved. Acetone (630 g) was added to each container and agitated for 15 minutes. Isopropanol (630 g per container) was added to each container and agitation continued for 20 min. The contents were centrifuged at 5300 RCF at 15° C., for 1 h. The supernatants were discarded and each pellet was dissolved in water by adding LE water (100 g) followed by agitation at ambient. The solutions were transferred to a Lyoguard tray and bottles were rinsed with more LE water (66 g each) and the rinses were transferred to the same tray. The product was freeze-dried by setting the shelf temperature at −0.5° C. for 16-20 h and then at 20° C. until dry. Freeze-dried product was sampled for analytical and retention. The Lyoguard Tray was double-bagged, labelled and stored in the freezer (≤−15° C.). The potency of freeze-dried product was determined using qHNMR. This procedure afforded Crude Penta Dimer 17. Expected Yield: 26.1-35.5 g (61-83%).

Figure 2:
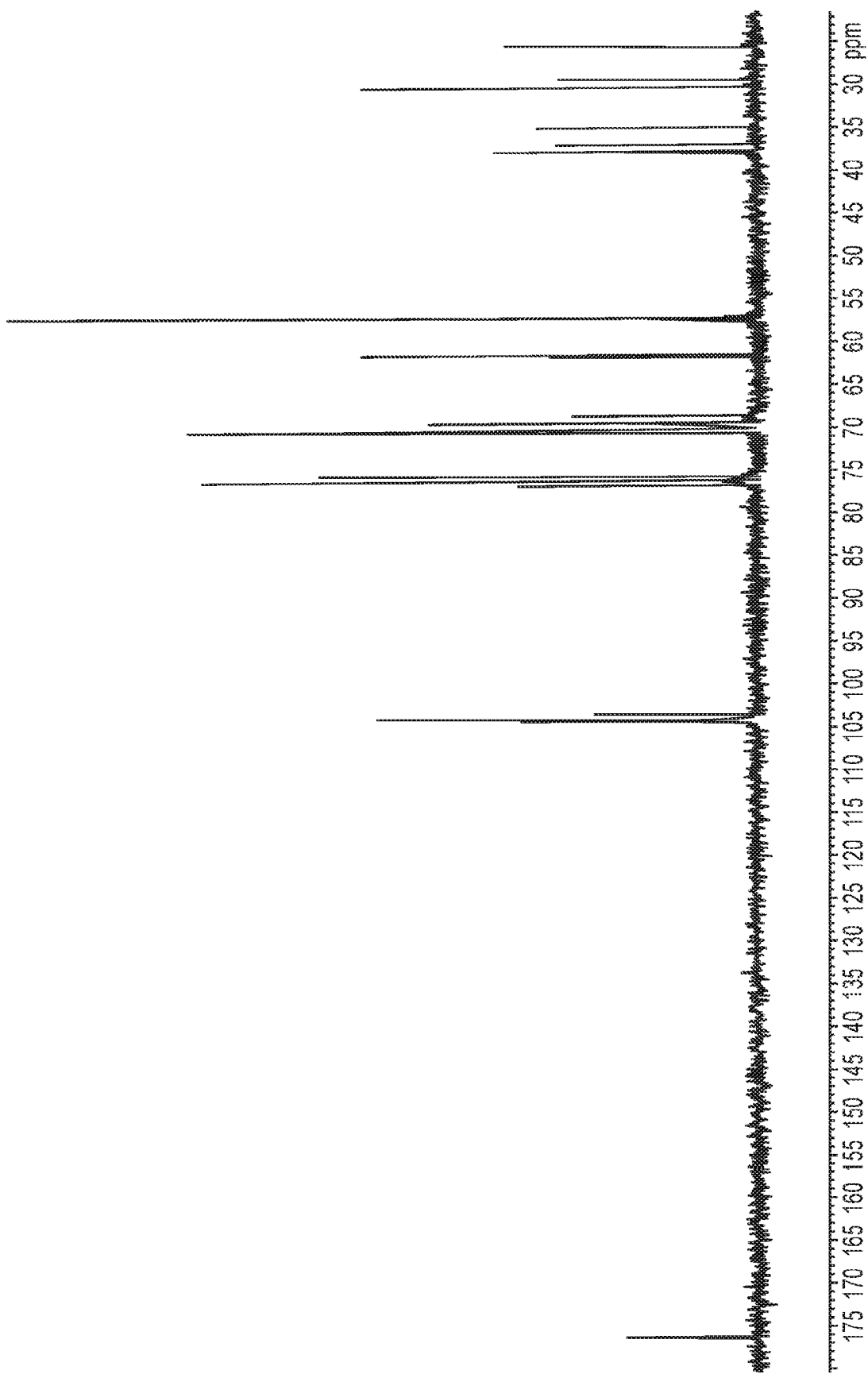
FIG. 2 illustrates the $^{13}$C NMR for compound 17.
Figure 3:
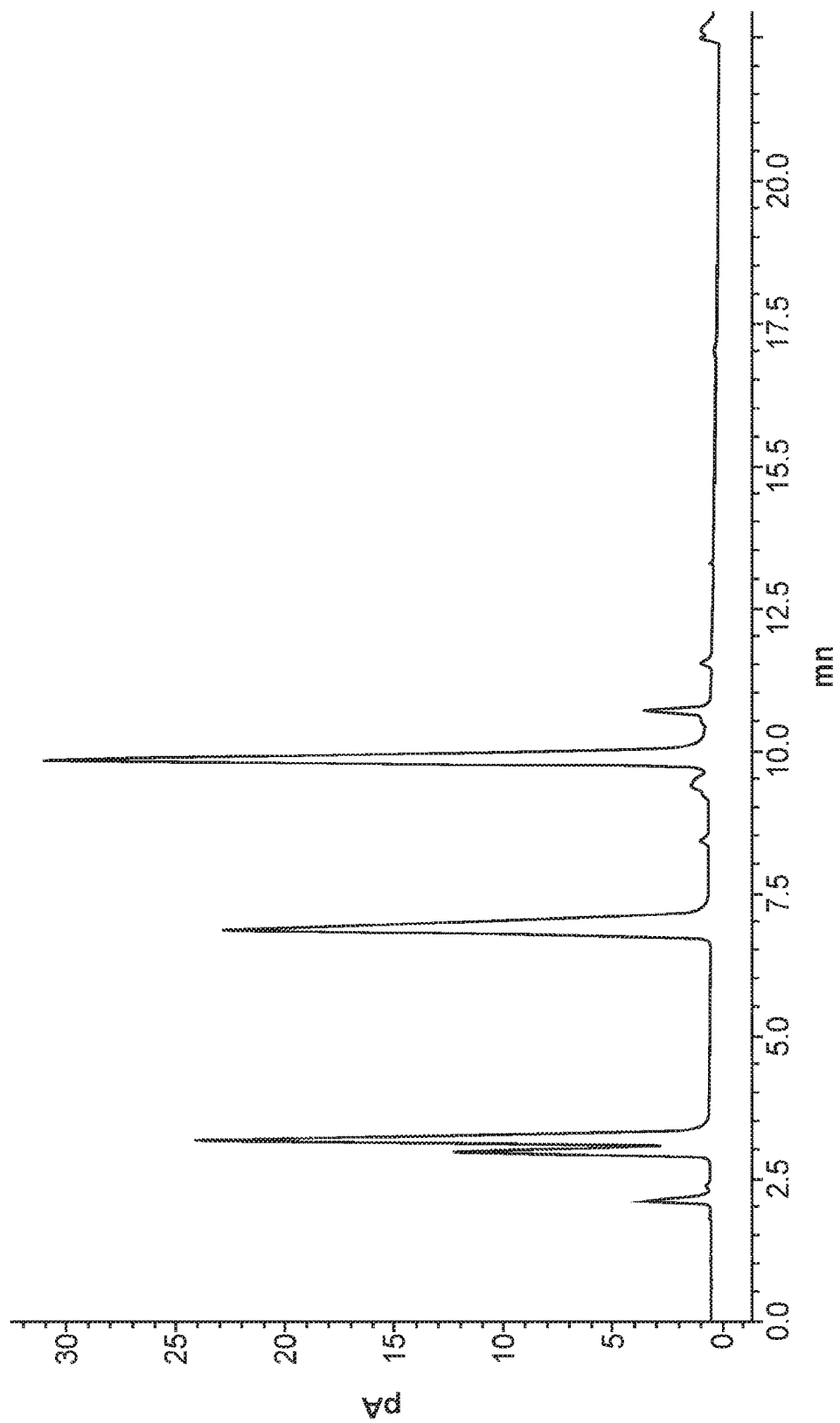
FIG. 3 provides a HPLC trace of the conversion of the disulfide, compound 16, to two equivalents of the monosulfide, compounds 17.

The identity of the compound 17 was determined by $^1$H and $^{13}$C NMR using a 500 MHz instrument. A reference solution of t-butanol was prepared at 25 mg/mL in D20. Samples were prepared at 13 mg/mL in D20 and the reference solution is added to the sample. The composition of the final test sample was 10 mg/mL of the Penta Dimer and 5 mg/mL of t-butanol. The $^1$H and $^{13}$C spectra were acquired and integrated. The resulting chemical shifts were assigned by comparison to theoretical shifts. The $^1$H NMR and $^{13}$C NMR spectra are shown in FIGS. 1 and 2 respectively.

Example 5—Conversion of Crude Penta Dimer to Free Base Form

Amberlite FPA91 (1.46 kg; 40 g/g of Crude Penta Dimer—corrected for potency) was charged to a large column. A solution of 8 L of 1.0 M NaOH was prepared by adding NaOH (320 g) to LE water (8.00 kg) in a 10 L Schott Bottle. This solution was passed through Amberlite resin over a period of 1 hour. LE water (40.0 kg) was passed through the Amberlite resin. The resin was flushed with additional LE water (~10 kg aliquots) until a pH of <8.0 was attained in the flow-through. The crude Penta Dimer (49 g, PN0704), stored in a Lyoguard tray, was allowed to warm to ambient temperature. LE water (400 g) was added to the Lyoguard tray containing Crude Penta Dimer (49 g) and allowed to fully dissolve before transferring to a 1 L Schott bottle. The tray was rinsed with a further charge of LE water (200 g) and these washings were added to the Schott bottle contents. The Crude Penta Dimer solution was carefully poured onto the top of the resin. The 1 L Schott bottle was rinsed with LE water (200 g) and loaded this onto the resin. The Amberlite tap was opened to allow the Crude Penta Dimer solution to move slowly into the resin over ~5 min. The tap was stopped and material left on the resin for ~10 min. LE water was poured onto the top of the resin. The tap was opened and eluted with LE water, collecting approximately 16 fractions of 500 mL. Each fraction was analyzed by TLC charring (10% $H_2SO_4$ in EtOH). All carbohydrate containing fractions were combined and filtered through a Millipore filter using a 0.2 μm nylon filter membrane. The solution was divided equally between 5-6 Lyoguard trays. The filtration vessel was rinsed with LE water (100 g) and divided between the trays. The material was freeze dried in the trays. The shelf temperature was set at −10° C. for 16-20 hr and then at +10° C. until the material was dry. LE water (150 g) was charged to all but one of the Lyoguard trays and transferred this into the one remaining tray containing dried material. Each of the empty trays was rinsed with a further charge of LE water (100 g) and this rinse volume was added to the final Lyoguard tray. The final Lyoguard tray was freeze dried. The shelf temperature was set at −10° C. for 16-20 hr and then at +10° C. until the materials dry. The product was sampled for analytical and retention. Dried material was transferred to HDPE or PP containers and stored at ≤−15° C. Expected yield: 31-34 g (86-94%).

TCEP reduction of the disulfide bond in the dimer is rapid and nearly stoichiometric. Use of a stoichiometric reduction with TCEP afforded approximately 2 equivalents of glucosamine pentasaccharide monomer. Specifically, the pentasaccharide dimer was dissolved in reaction buffer (50 mM HEPES buffer (pH 8.0)) containing 1 molar equivalent of TCEP. After 1 hour at ambient temperature, the reaction was analyzed by HPLC with CAD detection. Under these conditions, conversion to the penta-glucosamine monomer (peak at ~10 minutes) was nearly complete (penta glucsamine dimer peak at ~11.5 minutes)—See FIG. 4. The remaining unannotated peaks were derived from the sample matrix. Based on the balanced chemical equation, the added TCEP was largely converted to TCEP oxide and any residual TCEP inhibited air oxidation back to the dimer prior to addition to the conjugation reaction. For simplicity, glucosamine pentasaccharide can be added based on input dimer and assuming >95% conversion to the monomer under these conditions.

The identity of the Penta Dimer was determined by $^1$H and $^{13}$C NMR using a 500 MHz instrument. A reference solution of t-butanol was prepared at 25 mg/mL in D20. Samples were prepared at 13 mg/mL in D20 and the reference solution was added to the sample. The composition of the final test sample was 10 mg/mL of the Penta Dimer and 5 mg/mL of t-butanol. The $^1$H and $^{13}$C spectra were acquired and integrated. The resulting chemical shifts are assigned by comparison to theoretical shifts. $^1$H and $^{13}$C NMR spectra are shown in FIGS. 1 and 2 respectively.

Example 5—Conversion to the Penta Saccharide Monomer of Example 4 with the TT-Linker of Example 2 to Provide for a Vaccine of this Invention (Compound 18)

The TT monomer-linker intermediate of Example 2 was reacted with increasing concentrations of 4-70 pentameric glucosamine molar equivalents (2-35 pentasaccharide dimer molar equivalents) for 4 hours at ambient temperature. The crude conjugates from each titration point were purified by partitioning through a 30 kDa MWCO membrane. Each purified conjugate sample was analyzed for protein content, payload density by SEC-MALS and monomer/aggregate content by SEC HPLC. The data showed saturation of the payload density at 50 pentameric glucosamine equivalents. Based on the SEC HPLC analysis, the aggregate content increased as the pentasaccharide monomer charge was increased and appeared to reach steady state levels of an approximately 4% increase starting at 30 pentameric glucosamine equivalents. Based on these results, the pentasaccharide dimer charge selected for subsequent conjugation reactions was 25 molar equivalents, corresponding to a theoretical charge of 50 molar equivalents of pentameric glucosamine.

A series of three trial syntheses followed by a GMP synthesis of compound 18 were prepared as per above. Each of the resulting products was evaluated for potency (by ELISA assay) and payload density (molar ratio of pentameric glucosamine to tetanus toxoid). The following table provides the results.

|  | Trial No. 1 | Trial No. 2 | Trial No. 3 | GMP Run |
| --- | --- | --- | --- | --- |
| Payload Density of Compound 18 | 35 | 38 | 36 | 35 |
| Potency of Compound 18 | 94% | 101% | 87% | 98% |

These results evidence very high loading factors for the compounds of this invention. The foregoing description has been set forth merely to illustrate the invention and is not meant to be limiting. Since modifications of the described embodiments incorporating the spirit and the substance of the invention may occur to persons skilled in the art, the invention should be construed broadly to include all variations within the scope of the claims and equivalents thereof.

Example 6 Tetanus Toxoid Purification by Size Exclusion Chromatograpy

Aliquots of concentrated Tetanus Toxoid were purified by chromatography on a GE Healthcare 2.6×60 cm Superdex 200 column eluting with 10 mM NaHCO$_3$/150 mM NaCl (pH 9.0) at 2.0 mL/minute. Individual fractions (4.0 mL) were pooled based on analytical SEC-HPLC testing. Based on the purity of the TT-monomer preparation obtained under these conditions (2.0 mL sample/0.6% of bed volume), the Superdex 200 charge volume was successfully increased by a factor of 2 (4.0 mL sample/1.2% of bed volume) without significant change to the resolution. This change effectively reduced the number of chromatography cycles required for purification. The SEC pool containing desired quality of TT-monomer was concentrated/buffer exchanged using the Amicon Ultra-15 Ultracel 30 kDa regenerated cellulose centrifugal filters. The purified TT was buffer exchanged into 50 mM HEPES (pH 8.0) buffer for conjugation studies.

What is claimed is:

1. A composition comprising a pharmaceutically acceptable excipient and an effective amount of a conjugate of formula $$(A-B)_x-C \qquad \qquad I$$

where A comprises from 3 to 12 repeating β-(1→6)-glucosamine units or mixtures thereof having the formula:

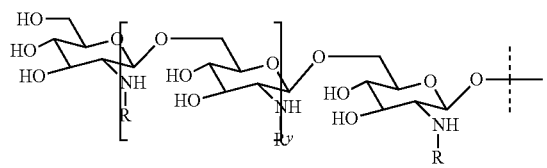

B is of the formula:

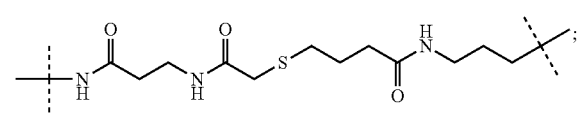

wherein each unit (A-B)- of (A-B) x is attached to C via the amide nitrogen of B indicated at the vertical dashed line of B; and
C is tetanus toxoid;
x is an integer from at least about 10 to about 40;
y is an integer from 1 to 10; and
R is hydrogen or acetyl provided that no more than 40% of the R groups are acetyl;
wherein said composition comprises less than 3 weight percent of detectable impurities having a molecular weight of less than 50,000; and
further wherein said composition comprises monomeric and dimeric toxoid with less than 5 percent of detectable higher oligomers.

2. The composition of claim 1, wherein R is hydrogen.

3. The composition of claim 2, wherein y is 3.

4. The composition of claim 3, wherein x is at least 25.

5. The composition of claim 1, wherein said composition is maintained at a temperature to inhibit oligomerization of the toxoid.

6. The composition of claim 5, wherein the composition is maintained at a temperature to not induce denaturation.

7. The composition of claim 1, wherein said composition comprises no more than about 0.5 weight percent of oligosaccharide-linked contaminants having a particle size of less than 1 micron wherein said weight percent is based on the weight of a vaccine compound.

8. The composition of claim 1 wherein said conjugate is selected from:

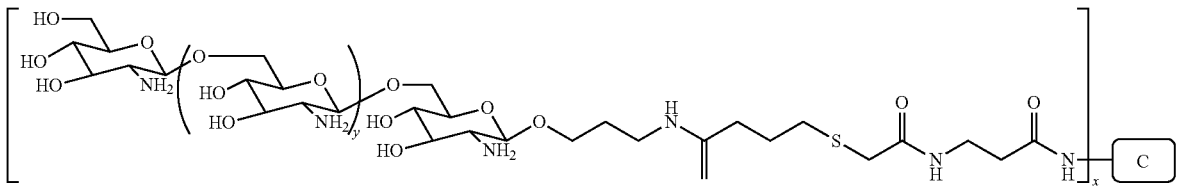

where x is 10, y is 2, C is tetanus toxoid.

9. The composition of claim 1 wherein said conjugate is selected from:

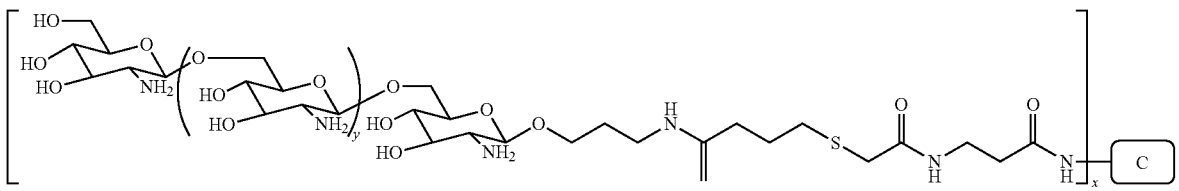

where x is 15, y is 3, C is tetanus toxoid.

10. The composition of claim 1 wherein said conjugate is selected from:

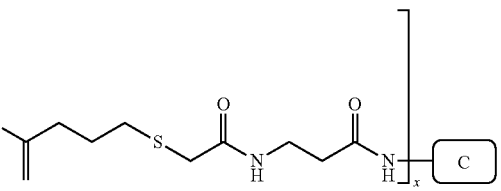

where x is 40, y is 3, C is tetanus toxoid.

* * * * *